US011365200B2

(12) United States Patent
Lin et al.

(10) Patent No.: US 11,365,200 B2
(45) Date of Patent: Jun. 21, 2022

(54) ATF3 INDUCTION COMPOUNDS

(71) Applicants: TAIPEI MEDICAL UNIVERSITY, Taipei (TW); NATIONAL RESEARCH INSTITUTE OF CHINESE MEDICINE, MINISTRY OF HEALTH AND WELFARE, Taipei (TW); ACADEMIA SINICA, Taipei (TW); BUDDHIST TZU CHI MEDICAL FOUNDATION, Hualien (TW)

(72) Inventors: Heng Lin, Taipei (TW); Ming-jaw Don, Taipei (TW); Ching-feng Cheng, New Taipei (TW); Jing-jy Cheng, New Taipei (TW); Wen-shan Li, Taipei (TW); Hui-chen Ku, Taoyuan (TW); Hsiao-fen Li, Tainan (TW); Hsi-hsien Chen, New Taipei (TW); W J Huang, Taipei (TW)

(73) Assignees: TAIPEI MEDICAL UNIVERSITY, Taipei (TW); NATIONAL RESEARCH INSTITUTE OF CHINESE MEDICINE, MINISTRY OF HEALTH AND WELFARE, Taipei (TW); ACADEMIA SINICA, Taipei (TW); BUDDHIST TZU CHI MEDICAL FOUNDATION, Hualien (TW)

( * ) Notice: Subject to any disclaimer, the term of this patent is extended or adjusted under 35 U.S.C. 154(b) by 0 days.

(21) Appl. No.: 16/496,376

(22) PCT Filed: Mar. 22, 2018

(86) PCT No.: PCT/CN2018/080086
§ 371 (c)(1),
(2) Date: Sep. 20, 2019

(87) PCT Pub. No.: WO2018/171688
PCT Pub. Date: Sep. 27, 2018

(65) Prior Publication Data
US 2020/0361950 A1  Nov. 19, 2020

Related U.S. Application Data

(60) Provisional application No. 62/474,869, filed on Mar. 22, 2017.

(51) Int. Cl.
| | |
|---|---|
| C07D 493/04 | (2006.01) |
| C07D 495/04 | (2006.01) |
| A61K 31/366 | (2006.01) |
| A61K 31/381 | (2006.01) |
| A61P 3/10 | (2006.01) |
| A61P 3/04 | (2006.01) |
| C07D 491/153 | (2006.01) |
| A23L 33/10 | (2016.01) |
| C07D 491/052 | (2006.01) |
| C07D 495/14 | (2006.01) |

(52) U.S. Cl.
CPC .......... *C07D 491/153* (2013.01); *A23L 33/10* (2016.08); *A61P 3/04* (2018.01); *A61P 3/10* (2018.01); *C07D 491/052* (2013.01); *C07D 493/04* (2013.01); *C07D 495/04* (2013.01); *C07D 495/14* (2013.01)

(58) Field of Classification Search
CPC .. C07D 493/04; C07D 495/04; A61K 31/366; A61K 31/381; A61P 3/04; A61P 3/10
See application file for complete search history.

(56) References Cited

U.S. PATENT DOCUMENTS

| | | | | |
|---|---|---|---|---|
| 7,208,518 B2* | 4/2007 | Mercep | ............ | A61P 17/02 514/453 |
| 7,495,026 B2* | 2/2009 | Lee | ............ | C07D 493/04 514/453 |
| 2010/0029760 A1 | 2/2010 | Kwak et al. | | |

FOREIGN PATENT DOCUMENTS

| | | |
|---|---|---|
| CN | 102115732 A | 7/2011 |
| CN | 102702303 A | 10/2012 |
| CN | 104415028 A | 3/2015 |
| CN | 102579460 B | 4/2015 |
| WO | 2005087225 A1 | 9/2005 |
| WO | 2015/081199 A1 | 6/2015 |

OTHER PUBLICATIONS

Wang et al. (Journal of Medicinal Chemistry (2004), 47(23), 5816-5819). Abstract. (Year: 2004).*
Seo et al. (Phytochemistry (2000), 55(1), 35-42). Abstract. (Year: 2000).*
Dong et al. (Journal of Medicinal Chemistry (2010), 53(5), 2299-2308).*
Extended European Search Report in EP Application No. 18771947.1 dated Aug. 31, 2020, in 10 pages.
Yilmaz, Mehmet, et al. "Synthesis of 2, 3-Dihydro-4 H-furo [3, 2-c] chromen-4-ones and 2, 3-Dihydronaphtho [2, 3-b] furan-4, 9-diones by the Radical Cyclizations of Hydroxyenones with Electron-Rich Alkenes using Manganese (III) Acetate." Synthetic Communications 38.6 (2008): 914-927.
Liu, Tao, et al. "Sesquiterpenoids with Anti-MDR *Staphylococcus aureus* Activities from Ferula ferulioides." Chemistry & Biodiversity 12.4 (2015): 599-614.

(Continued)

*Primary Examiner* — Bruck Kifle
(74) *Attorney, Agent, or Firm* — Duane Morris LLP

(57) ABSTRACT

The invention relates to compounds for treating and/or preventing obesity and obesity-related disorders. Particularly, the invention provides chromanone derivatives used as ATF3 inducer and for treating and/or preventing obesity and obesity-related disorders such as heart disease, hypertension, hyperlipidemia and diabetes.

10 Claims, 15 Drawing Sheets

(56) References Cited

OTHER PUBLICATIONS

Sato, Eisuke, et al. "Photochemistry of Conjugated Nitrogen-Thiocarbonyl Systems. VII.: Photoaddition of Quinoline-, Isoquinoline- and Phthalazine-Thione Systems to Olefins." Chemical and Pharmaceutical Bulletin 38.5 (1990): 1205-1210.

Kinder, Michael A., et al. "Photocycloaddition of Isocoumarins and Isothiocoumarins to Alkenes." Helvetica Chimica Acta 84.8 (2001): 2373-2378.

Saidi, Mohammad R., and Fatemeh Rajabi. "Microwave and BF3 promoted rearrangement of allyloxycoumarins to allylcoumarins and dihydrofurocoumarins." Heterocycles 55.9 (2001): 1805-1812.

Wu, Chun-yan et al. "Cytotoxic diterpenoids from Salvia yunnanensis" Phytochemistry, vol. 106, Jul. 28, 2014 (Jul. 28, 2014), 171-177.

Zhang, De-Wu et al. "Two new diterpenoids from cell cultures of Salvia miltiorshiza" Chemical & Pharmaceutical Bulletin, vol. 61, No. 5, Dec. 31, 2013 (Dec. 31, 2013), 576-580.

Ghosh, Ketaki et al. "Total Synthesis of Neo-Tanshinlactones through a Cascade Benzannulation-Lactonization as the Key Step" Eur. J. Org. Chem., May 8, 2013 (May 8, 2013), 4037-4046.

Dong, Yizhou et al. "Anti tumor agents 269. Non-aromatic ring-A neotanshinlactone analog, TNO, as a new class of potent anti tumor agents" Bioorganic & Medicinal Chemistry Letters, vol. 19, Sep. 29, 2009 (Sep. 29, 2009), 6289-6292.

International Search Report in International Patent Application No. PCT/CN2018/080086, dated Jun. 22, 2018, in 6 pages.

Jang, Min-Kyung et al. "ATF3 plays a role in adipocyte hypoxia-mediated mitochondria dysfunction in obesity." Biochemical and Biophysical Research Communications 431.3 (2013): 421-427.

Hu, Ping, et al. "Minimally invasive aortic banding in mice: effects of altered cardiomyocyte insulin signaling during pressure overload." American Journal of Physiology—Heart and Circulatory Physiology 285.3 (2003): H1261-H1269.

Office Action in Taiwan Counterpart Application No. 107109915, dated Jan. 2, 2019, in 6 pages; English translation provided.

Mingzhao Dong "Study on the total synthesis of salviatrinone-M, salviatrinone-N and dihydroneotanshinlactone", National Institute of Chinese Medicine Research Report, 2006, Project No. NRICM-95-DMC-06, 12 pages; English translation provided.

* cited by examiner

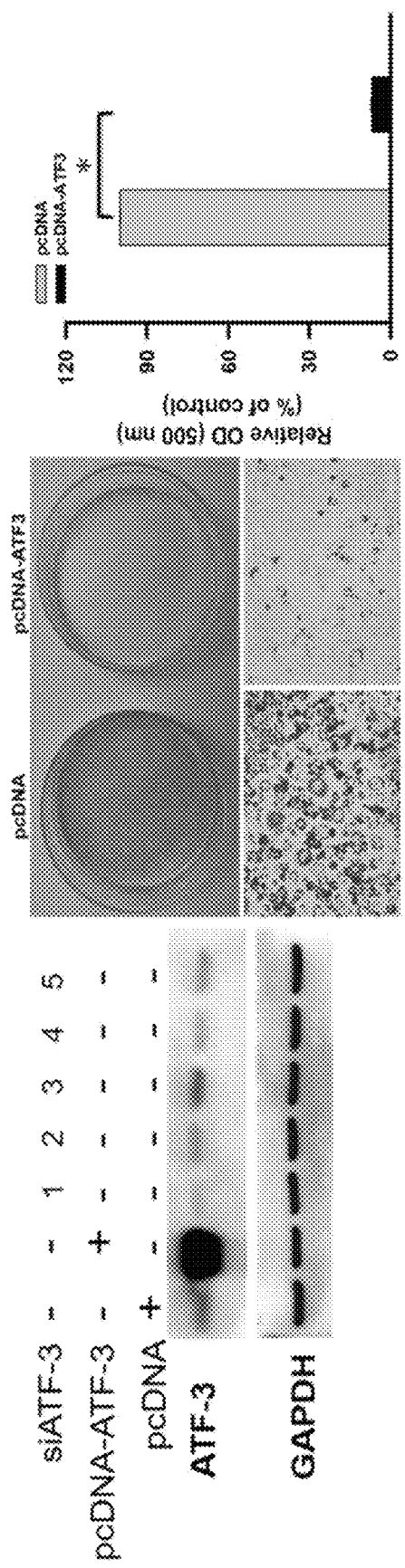

ATF3 INDUCTION COMPOUNDS

This application claims priority to International Patent Application No. PCT/CN2018/080086, filed Mar. 22, 2018, which claims the benefit of U.S. Provisional Application No. 62/474,869, filed on Mar. 22, 2017, both of which are incorporated herein in their entirety by reference.

FIELD OF THE INVENTION

The invention relates to compounds for treating and/or preventing obesity and obesity-related disorders. Particularly, the invention provides chromenone derivatives used as ATF3 inducer and for treating and/or preventing obesity and obesity-related disorders such as heart disease, hypertension, hyperlipidemia and diabetes.

BACKGROUND OF THE INVENTION

Obesity refers to a condition where excess fatty tissue is accumulated in the body due to genetic, environmental, and psychological factors, which results in health disorders, and may cause serious health problems such as hypertension, hyperlipidemia, heart disease, diabetes, cancer, etc. Obesity considerably increases the risk of developing cardiovascular diseases as well. Coronary insufficiency, atheromatous disease, and cardiac insufficiency are foremost among the cardiovascular complications induced by obesity. There are no real treatments based on the biology of the primary metabolic abnormalities found in obesity and its related conditions, such as metabolic syndrome or atherosclerosis.

Activating transcription factor 3 (ATF3) is a member of the ATF/cyclic AMP response element-binding (ATF/CREB) family of transcription factors. KR1556439 B1 provides a pharmaceutical composition for preventing, treating and screening mitochondrial dysfunction-related diseases (such as hypertension, obesity, insulin resistance, fatty liver, liver fibrosis, metabolic syndrome, neurodegenerative disorder, bipolar disorder, diabetes, ischemia, cardiac failure, cancer and cardiovascular disease), and comprises a promoter activity or expression of one or more transcription factors including ATF3. A study suggests that ATF3 may play a role in adipocyte hypoxia-mediated mitochondrial dysfunction in obesity (Biochem Biophys Res Commun. 2013 Feb. 15; 431(3):421-7).

Accordingly, there is still a need for new compounds for treatment of individuals suffering from obesity and obesity-related disorders.

SUMMARY OF THE INVENTION

The disclosure is directed to chromenone derivatives used as an ATF3 inducer compound and for treating and/or preventing obesity and obesity-related disorders. The compounds of this disclosure are obtained by: (1) transfecting a special DNA sequence of ATF3 (pGL4-ATF3) into 3T3-L1 preadipocytes and H9C2 cardiomyocytes; (2) using the stable clone as a platform for screening of drug for anti-obesity, anti-atherosclerosis, anti-cardiovascular disease and promotion of white-to-brown adipocyte transdifferentiation; and (3) using the platform for special drug screening. The invention successfully screens drugs based on induction of the above-mentioned ATF3 expression and the drugs include, but are not limited to, ST32c, ST32da, ST32db and their derivatives. The invention further finds that these compounds have an inhibitory effect on obesity and obesity-induced diabetes and a facilitatory effect on white-to-brown adipocyte transdifferentiation, thereby increasing the body energy expenditure and suppressing diabetes. In addition, these compounds also can inhibit high blood pressure or hypoxia induced cardiomyopathy to increase heart function.

Accordingly, the present invention provides a compound having formula (I) as disclosed herein.

The present invention also provides a pharmaceutical composition comprising the compound disclosed herein.

The present invention also provides a method for treating and/or preventing obesity, obesity-induced diabetes, inhibit high blood pressure or hypoxia induced cardiomyopathy thereby increasing heart function, comprising administering an effective amount of the compound disclosed herein to a subject.

The present invention also provides a method of for selecting AT3 inducer as an anti-obesity agent, an anti-atherosclerosis agent or an anti-cardiovascular agent, comprising contacting a compound with a cell transfected with a recombinant ATF3 and detecting ATF3 expression of the cell and determining whether the compound is an AT3 inducer when the cell expresses a protein transcribed from AT3.

DETAILED DESCRIPTION OF THE INVENTION

Figure 1A:
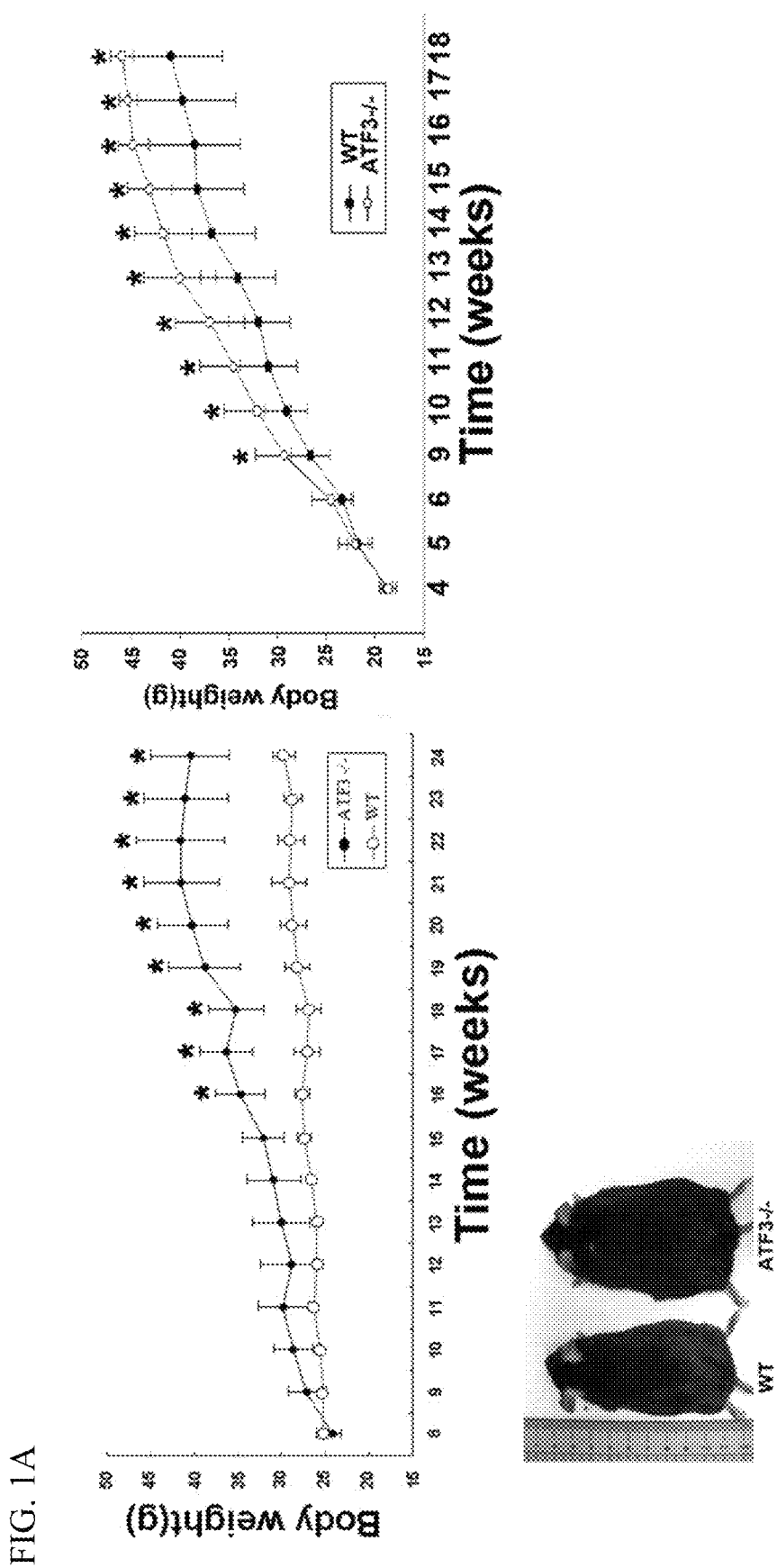
FIGS. 1 (A) to (E) show that ATF3 prevents diet-induced obesity and metabolic dyshomeostasis. Mice were fed control or a HFD for 12 or 16 weeks. (A) Body weight changes of wild-type (WT) and ATF3−/− mice fed a normal diet (ND) (left panel) or high fat diet (HFD) (right panel), (n=8 animals/group). (B) Serum triglyceride level (12-week HFD). (C) Weight difference between white adipose tissue (WAT) and brown adipose tissue (BAT). (D) Histology of epididymal WAT, adipocyte diameter and size. Scale bar=100 (n=6 per group). (E) Photograph of liver by Oil Red O-staining (8-week HFD).

The invention is based on the discovery of a series of ATF3 inducers and their effect in treating and/or preventing obesity and obesity-related disorders such as heart disease, hypertension, hyperlipidemia and diabetes. ATF3 has a short half-life and is a downstream gene, so the side effect of ATF3 is low and the appetite will not be inhibited. The compounds of the invention have an inhibitory effect on obesity and obesity-induced diabetes and a facilitatory effect on white-to-brown adipocyte transdifferentiation, which thus increase the body energy expenditure and suppress diabetes. In addition, these compounds also can inhibit high blood pressure or hypoxia induced cardiomyopathy, thereby increasing heart function.

Definitions

Unless otherwise stated, the following terms used in this application, including the specification and claims, have the definitions given below. It must be noted that, as used in the specification and the appended claims, the singular forms "a", "an," and "the" include plural referents unless the context clearly dictates otherwise.

As used herein, the term "prodrug" as used in this application refers to a precursor or derivative form of a compound of the disclosure that may be less cytotoxic to cells compared to the parent compound or drug and is capable of being enzymatically or hydrolytically activated or converted into the more active parent form.

As used herein, the term "unsaturated" means that a moiety has one or more units of unsaturation.

As used herein, the term "substituted" as used herein means that any one or more hydrogens on the designated atom, radical or moiety is replaced with a selection from the indicated group, provided that the atom's normal valence is not exceeded, and that the substitution results in an acceptably stable compound.

As used herein, the term "pharmaceutically acceptable" is employed herein to refer to those compounds, materials, compositions, and/or dosage forms which are, within the scope of medical judgment, suitable for use in contact with the tissues of human beings and animals without excessive toxicity, irritation, allergic response, or other problem or complication, and commensurate with a reasonable benefit/risk ratio.

As used herein, "pharmaceutically acceptable salts" refers to derivatives of the disclosed compounds wherein the parent compound is modified by making acid or base salts thereof. Examples of pharmaceutically acceptable salts include, but are not limited to, mineral or organic acid salts of basic residues such as amines, pyridine, pyrimidine and quinazoline; alkali or organic salts of acidic residues such as carboxylic acids; and the like.

As used herein, the term "stereoisomer" is a general term for all isomers of individual molecules that differ only in the orientation of their atoms in space. It includes enantiomers and isomers of compounds with more than one chiral center that are not mirror images of one another (diastereoisomers).

As used herein, the term "chiral center" refers to a carbon atom to which four different groups are attached.

As used herein, the terms "enantiomer" and "enantiomeric" refer to a molecule that cannot be superimposed on its mirror image and hence is optically active, wherein the enantiomer rotates the plane of polarized light in one direction and its mirror image compound rotates the plane of polarized light in the opposite direction.

As used herein, the term "racemic" refers to a mixture of equal parts of enantiomers that is optically inactive.

As used herein, the term "resolution" refers to the separation or concentration or depletion of one of the two enantiomeric forms of a molecule.

As used herein, the term "alkyl," employed alone or in combination with other terms, refers to a saturated hydrocarbon group that may be straight-chain or branched. In some embodiments, the alkyl group contains 1 to 6, 1 to 4, or 1 to 3 carbon atoms. Examples of alkyl moieties include, but are not limited to, chemical groups such as methyl, ethyl, n-propyl, isopropyl, n-butyl, isobutyl, sec-butyl, tert-butyl, n-pentyl, 2-methyl-1-butyl, 3-pentyl, n-hexyl, 1,2,2-trimethylpropyl, and the like. In some embodiments, the alkyl group is methyl, ethyl, or propyl.

As used herein, "alkenyl," employed alone or in combination with other terms, refers to an alkyl group having one or more carbon-carbon double bonds. In some embodiments, the alkenyl moiety contains 2 to 6 or 2 to 4 carbon atoms. Example alkenyl groups include, but are not limited to, ethenyl, n-propenyl, isopropenyl, n-butenyl, sec-butenyl, and the like As used herein, "alkynyl," employed alone or in combination with other terms, refers to an alkyl group having one or more carbon-carbon triple bonds. In some embodiments, the alkynyl moiety contains 2 to 6 or 2 to 4 carbon atoms. Example alkynyl groups include, but are not limited to, ethynyl, propyn-1-yl, propyn-2-yl, and the like.

As used herein, "halo" or "halogen," employed alone or in combination with other terms, includes fluoro, chloro, bromo, and iodo. In some embodiments, halo is F, Cl or Br.

As used herein, the term "haloalkyl" means a substituted alkyl having one or more halo substituents. For example, "haloalkyl" includes mono, di, and trifluoromethyl.

As used herein, the term "haloalkoxy" means an alkoxy group having one or more halo substituents.

As used herein, the terms "alkoxy" and "alkyloxy," which may be used interchangeably, mean a moiety of the formula —OR, wherein R is an alkyl moiety as defined herein. Examples of alkoxy moieties include, but are not limited to, methoxy, ethoxy, isopropoxy, and the like.

As used herein, the term "alkenoxy" group used either alone or in combination with other radicals, is selected from groups containing an alkenyl radical, as defined above, attached to an oxygen atom, more preferably selected from vinyloxy, allyloxy, butenoxy, pentenoxy, hexenoxy, and the like.

As used herein, the term "alkoxyalkyl" means a moiety of the formula Ra-O-Rb-, where Ra is alkyl and Rb is alkylene as defined herein. Exemplary alkoxyalkyl groups include, by way of example, 2-methoxyethyl, 3-methoxypropyl, 1-methyl-2-methoxyethyl, 1-(2-methoxyethyl)-3-methoxypropyl, and 1-(2-methoxyethyl)-3-methoxypropyl.

As used herein, the term "aryl" means a monovalent cyclic aromatic hydrocarbon moiety consisting of a mono-, bi- or tricyclic aromatic ring. The aryl group can be optionally substituted as defined herein. Examples of aryl moieties include, but are not limited to, phenyl, naphthyl, phenanthryl, fluorenyl, indenyl, pentalenyl, azulenyl, oxydiphenyl, biphenyl, methylenediphenyl, aminodiphenyl, diphenylsulfidyl, diphenyl sulfonyl, diphenylisopropylidenyl, benzodioxanyl, benzofuranyl, benzodioxylyl, benzopyranyl, benzoxazinyl, benzoxazinonyl, benzopiperadinyl, benzopiperazinyl, benzopyrrolidinyl, benzomorpholinyl, methylenedioxyphenyl, ethylenedioxyphenyl, and the like, including partially hydrogenated derivatives thereof, each being optionally substituted. In certain embodiments "aryl" means phenyl or naphthyl, each optionally substituted. In many embodiments "aryl" is optionally substituted phenyl.

As used herein, the term "heteroaryl" refers to a monocyclic or bicyclic radical of 5 to 12 ring atoms having at least one aromatic ring containing one, two, or three ring heteroatoms selected from N, O, or S, the remaining ring atoms being C, with the understanding that the attachment point of the heteroaryl radical will be on an aromatic ring. The heteroaryl ring may be optionally substituted as defined herein. Examples of heteroaryl moieties include, but are not limited to, optionally substituted imidazolyl, oxazolyl, isoxazolyl, thiazolyl, isothiazolyl, oxadiazolyl, thiadiazolyl, pyrazinyl, thienyl, benzothienyl, thiophenyl, furanyl, pyranyl, pyridyl, pyrrolyl, pyrazolyl, pyrimidyl, quinolinyl, isoquinolinyl, benzofuryl, benzothiophenyl, benzothiopyranyl, benzimidazolyl, benzooxazolyl, benzooxadiazolyl, benzothiazolyl, benzothiadiazolyl, benzopyranyl, indolyl, isoindolyl, triazolyl, triazinyl, quinoxalinyl, purinyl, quinazolinyl, quinolizinyl, naphthyridinyl, pteridinyl, carbazolyl, azepinyl, diazepinyl, acridinyl and the like, including partially hydrogenated derivatives thereof, each optionally substituted.

As used herein, the terms "cycloaliphatic," "carbocycle," "carbocyclyl," "carbocyclo," or "carbocyclic," used alone or as part of a larger moiety, refer to a saturated or partially unsaturated cyclic aliphatic monocyclic or bicyclic ring systems, as described herein, having from 3 to 10 members, wherein the aliphatic ring system is optionally substituted as defined above and described herein. Cycloaliphatic groups include, without limitation, cyclopropyl, cyclobutyl, cyclopentyl, cyclopentenyl, cyclohexyl, cyclohexenyl, cycloheptyl, cycloheptenyl, cyclooctyl, cyclooctenyl, and cyclooctadienyl. The terms "cycloaliphatic," "carbocycle," "carbocyclyl," "carbocyclo," or "carbocyclic" also include aliphatic rings that are fused to one or more aromatic or nonaromatic rings, such as decahydronaphthyl, tetrahydronaphthyl, decalin, or bicyclo[2.2.2]octane, where the radical or point of attachment is on an aliphatic ring.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position.

As used herein, the term "pharmaceutically acceptable salt" refers to a salt of a compound of the present invention. Suitable pharmaceutically acceptable salts include acid addition salts which may, for example, be formed by mixing a solution of compounds of the present invention with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, where the compound carries an acidic moiety, suitable pharmaceutically acceptable salts thereof may include alkali metal salts (e.g., sodium or potassium salts); alkaline earth metal salts (e.g., calcium or magnesium salts); and salts formed with suitable organic ligands (e.g., ammonium, quaternary ammonium and amine cations formed using counteranions such as halide, hydroxide, carboxylate, sulfate, phosphate, nitrate, alkyl sulfonate and aryl sulfonate). Illustrative examples of pharmaceutically acceptable salts include, but are not limited to, acetate, adipate, alginate, ascorbate, aspartate, benzenesulfonate, benzoate, bicarbonate, bisulfate, bitartrate, borate, bromide, butyrate, calcium edetate, camphorate, camphorsulfonate, camsylate, carbonate, chloride, citrate, clavulanate, cyclopentanepropionate, digluconate, dihydrochloride, dodecylsulfate, edetate, edisylate, estolate, esylate, ethanesulfonate, formate, fumarate, gluceptate, glucoheptonate, gluconate, glutamate, glycerophosphate, glycolylarsanilate, hemisulfate, heptanoate, hexanoate, hexylresorcinate, hydrabamine, hydrobromide, hydrochloride, hydroiodide, 2-hydroxy-ethanesulfonate, hydroxynaphthoate, iodide, isothionate, lactate, lactobionate, laurate, lauryl sulfate, malate, maleate, malonate, mandelate, mesylate, methanesulfonate, methylsulfate, mucate, 2-naphthalenesulfonate, napsylate, nicotinate, nitrate, N-methylglucamine ammonium salt, oleate, oxalate, pamoate (embonate), palmitate, pantothenate, pectinate, persulfate, 3-phenylpropionate, phosphate/diphosphate, picrate, pivalate, polygalacturonate, propionate, salicylate, stearate, sulfate, subacetate, succinate, tannate, tartrate, teoclate, tosylate, triethiodide, undecanoate, valerate, and the like.

As used herein, the term "solvates" means solvent addition forms that contain either stoichiometric or non-stoichiometric amounts of solvent. Some compounds have a tendency to trap a fixed molar ratio of solvent molecules in the crystalline solid state, thus forming a solvate. If the solvent is water the solvate formed is a hydrate; when the solvent is alcohol, the solvate formed is an alcoholate. Hydrates are formed by the combination of one or more molecules of water with one of the substances in which the water retains its molecular state as $H_2O$, such combination being able to form one or more hydrates.

The terms "disease" and "disorder" herein can be used interchangeably.

The terms "treatment" and "treating" embrace both preventative, i.e. prophylactic, or therapeutic, i.e. curative and/or palliative, treatment. Thus the terms "treatment" and "treating" comprise therapeutic treatment of patients having already developed said condition, in particular in manifest form. Therapeutic treatment may be symptomatic treatment in order to relieve the symptoms of the specific indication or causal treatment in order to reverse or partially reverse the conditions of the indication or to stop or slow down progression of the disease. Thus the compounds, compositions and methods of the present invention may be used for instance as therapeutic treatment over a period of time as well as for chronic therapy. In addition the terms "treatment" and "treating" comprise prophylactic treatment, i.e. a treatment of patients at risk to develop a condition mentioned hereinbefore, thus reducing said risk.

The term "therapeutically effective amount" means an amount of a compound of the present invention that (i) treats or prevents the particular disease or condition, (ii) attenuates, ameliorates, or eliminates one or more symptoms of the particular disease or condition, or (iii) prevents or delays the onset of one or more symptoms of the particular disease or condition described herein.

Compounds

In one aspect, the invention provides a compound of formula I shown below,

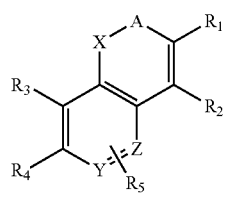

(I)

wherein
A is —C(=O)—, —C(=S)—, —NH—, —O— or —S—;
when A is —NH—, —O— or —S—, X is —C(=O)— or —C(=S)—; or when A is —C(=O)— or —C(=S)—, X is —NH—, —O—, —S— or —C(=O)—;
Y is absent or —C—, —N(R)—, —O— or —S—, R is hydrogen or alkyl;
when Y is absent, Z is —NH—, —O— or —S—; or when Y is —C—, —N(R)—, —O— or —S—, Z is —C— or —C(=O)—;
$R_1$ and $R_2$ are each independently H, $NH_2$, halogen, hydroxy, unsubstituted or substituted alkyl, unsubstituted or substituted haloalkyl, unsubstituted or substituted hydroxyalkyl, unsubstituted or substituted alkoxy, unsubstituted or substituted alkenoxy, unsubstituted or substituted alkoxyalkyl, unsubstituted or substituted alkenyl, unsubstituted or substituted alkynyl or unsubstituted or substituted aryl; or
  $R_1$ and $R_2$ are taken together with their intervening atoms to form an optionally substituted fused ring selected from a 5-7 membered saturated or partially unsaturated heterocyclic ring having 1-3 heteroatoms independently selected from nitrogen, oxygen, or sulfur;
$R_3$ and $R_4$ are each independently H, $NH_2$, halogen, hydroxy, unsubstituted or substituted alkyl, unsubstituted or substituted aryl, unsubstituted or substituted haloalkyl, unsubstituted or substituted hydroxyalkyl, unsubstituted or substituted alkoxyalkyl, unsubstituted or substituted alkenyl or unsubstituted or substituted alkynyl; or
  $R_3$ and $R_4$ are taken together with their intervening atoms to form an optionally substituted fused ring selected from a 5-8 membered saturated or partially unsaturated carbocyclic ring and 6-9 membered aromatic ring, or a 5-10 membered heteroaryl ring having 1 to 3 heteroatoms independently selected from nitrogen, oxygen, or sulfur; and
$R_5$ is H, halogen, —OH, —$NO_2$, alkyl, aryl, haloalkyl, hydroxyalkyl, alkoxy, alkoxyalkyl, alkenyl or alkynyl;
or a tautomer, enantiomer, stereoisomer thereof, or a solvate, prodrug or a pharmaceutically acceptable salt thereof.

In some embodiments of compounds of Formula (I), $R_1$ and $R_2$ are each independently $C_{1-6}$alkyl, $C_{1-6}$alkyl substituted by $C_{1-4}$alkyl, halo$C_{1-4}$alkyl or unsubstituted or substituted aryl. Preferably, $R_1$ is methyl, ethyl, isopropyl or $CF_3$. Preferably, the unsubstituted or substituted aryl is phenyl or benzyl.

In some embodiments of compounds of Formula (I), $R_1$ and $R_2$ are taken together with their intervening atoms to form an oxolane (tetrahydrofuran) ring, a dioxolane ring, a tetrahydrothiophene ring, a thiophene ring, an oxazole ring, a pyrrolidine ring, a pyrroline ring or a pyrazolidine ring, wherein the ring is unsubstituted or substituted by one or more substituents selected from alkyl, hydroxy, amino, nitro, halogen, haloalkyl, alkoxy or aryl. Preferably, the substituent alkyl is $C_{1-4}$ alkyl and the substituent alkyloxy is $C_{1-4}$alkyloxy. Preferably, the substituent haloalkyl is halo$C_{1-4}$alkyl, Preferably, the substituent aryl is phenyl or benzyl.

In some further embodiments, $R_1$ and $R_2$ are taken together with their intervening atoms to form an oxolane ring, a pyrroline ring or a thiophene ring, wherein the ring is unsubstituted or substituted by one or two alkyl (preferably, $C_{1-4}$alkyl), haloalkyl (preferably $C_{1-4}$haloalkyl, more preferably, —$CF_3$) or aryl (preferably phenyl or benzyl). In some embodiments, $R_1$ and $R_2$ are taken together with their intervening atoms to form an oxolane ring which unsubstituted or substituted by one or two methyl, ethyl, $CF_3$ or benzyl.

In some embodiments of compounds of Formula (I), $R_3$ and $R_4$ are each independently H or phenyl.

In some embodiments of compounds of Formula (I), $R_3$ and $R_4$ are taken together with their intervening atoms to form a fused cyclopentane ring, a fused cyclohexane ring or a fused cycloheptane ring; the fused ring is unsubstituted or substituted by $NH_2$, $NO_2$, halogen, hydroxy, unsubstituted or substituted alkyl, unsubstituted or substituted haloalkyl, unsubstituted or substituted hydroxyalkyl, unsubstituted or substituted alkoxy, unsubstituted or substituted alkoxyalkyl, unsubstituted or substituted alkenyl or unsubstituted or substituted alkynyl. In some further embodiments, $R_3$ and $R_4$ are taken together with their intervening atoms to form a fused cyclopentane ring, a fused cyclohexane ring, a fused cycloheptane ring, a fused cycloheptane ring wherein the ring is substituted by OH, $NO_2$, $NH_2$, $C_{1-4}$alkyloxy or halogen.

In some embodiments of compounds of Formula (I), $R_3$ and $R_4$ are taken together with their intervening atoms to form a fused benzene ring, a fused pyrrole ring, a fused furan ring, a fused thiophene ring, a fused pyridine ring, a fused benzofuran ring, a fused isobenzofuran ring, a fused indole ring, a fused isoindole ring or a fused benzothiophene ring; the ring is unsubstituted or substitute by $NH_2$, halogen, hydroxy, unsubstituted or substituted alkyl, unsubstituted or substituted haloalkyl, unsubstituted or substituted hydroxyalkyl, unsubstituted or substituted alkoxy, unsubstituted or substituted alkoxyalkyl, unsubstituted or substituted alkenyl or unsubstituted, substituted alkynyl, unsubstituted or substituted aryl or unsubstituted or substituted heteroaryl. In some further embodiments, $R_3$ and $R_4$ are taken together with their intervening atoms to form a fused benzene ring, a fused pyrrole ring, a fused furan ring, a fused thiophene ring, a fused pyridine ring, a fused benzofuran ring, a fused isobenzofuran ring, a fused indole ring, a fused isoindole ring, a fused benzothiophene ring or a fused benzene ring, the ring being substituted by OH, $NH_2$, $NO_2$, $C_{1-4}$alkyloxy, halogen or aryl (preferably pnehyl).

In some embodiments of compounds of Formula (I), $R_5$ is OH, $C_{1-4}$alkoxyl, $NO_2$, halogen, $C_{1-4}$alkyl or phenyl.

In some embodiments, the compound of Formula (I) is selected from the group consisting of:

(1) Substituted on A ring:

ST32da

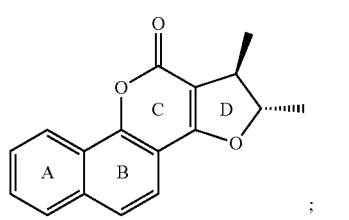

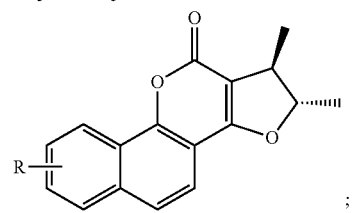

R = OH, OMe, NH2, F, Cl, Br, $NO_2$, Me, Et

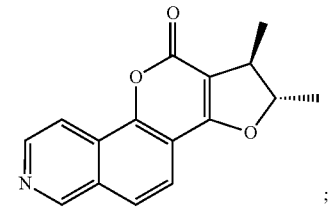

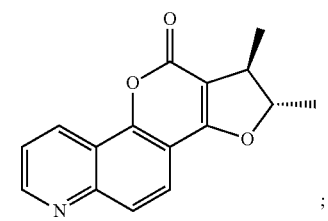

ST32db

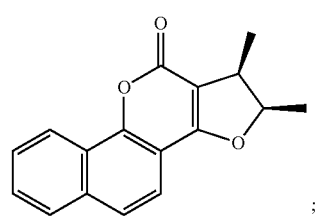

(2) A ring size and substitution:

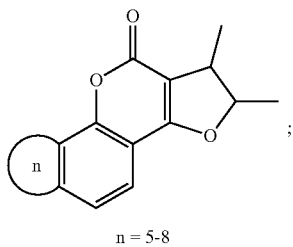

n = 5-8

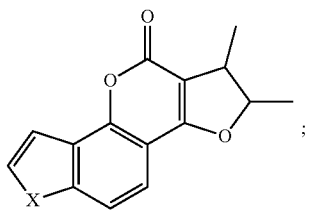

X = NH, O, S

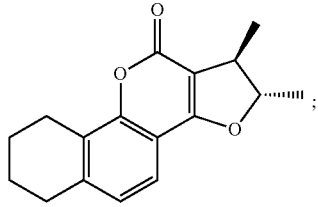

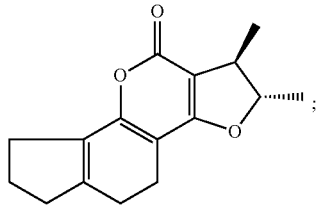

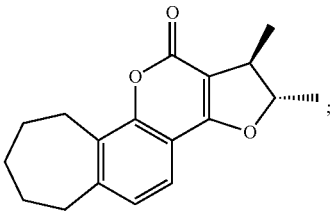

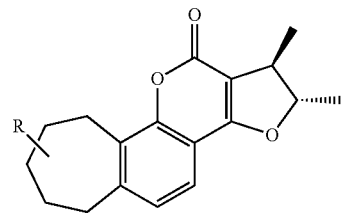

R = OH, OMe, NH2, F, Cl, Br, $NO_2$

ST32c

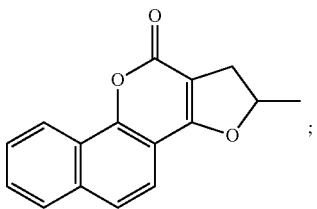

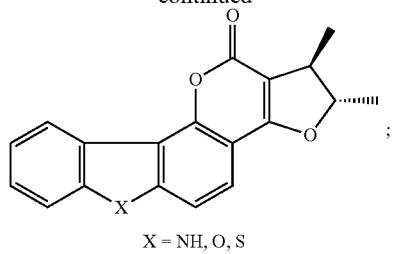
X = NH, O, S
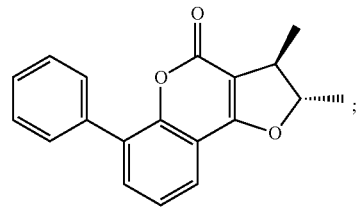
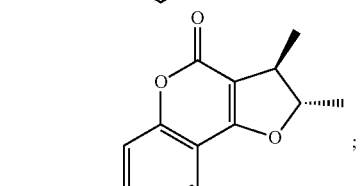
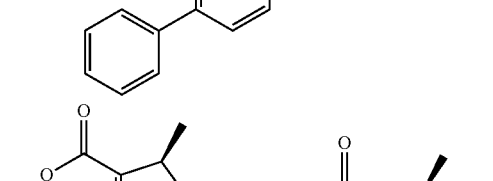
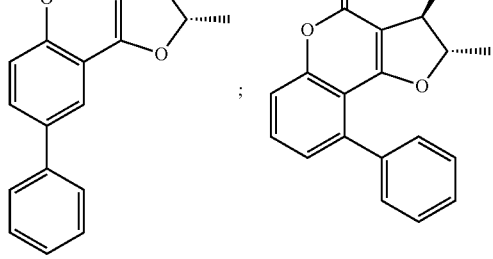
(3) B ring size and substitution:
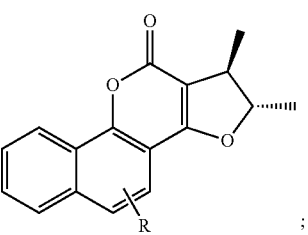
R = OH, OMe, NH2, F, Cl, Br, NO₂, Me, Et
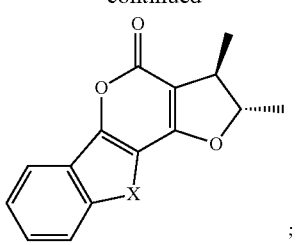
X = NH, O, S
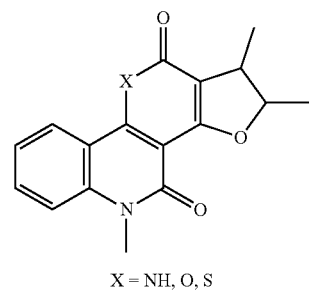
X = NH, O, S
(3) C ring size and substitution
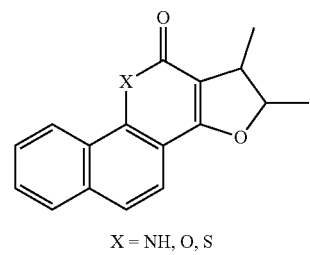
X = NH, O, S
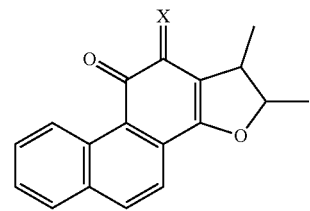
X = O, S
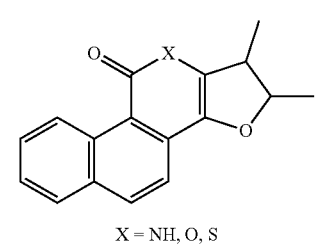
X = NH, O, S (4) D ring size and substitution:

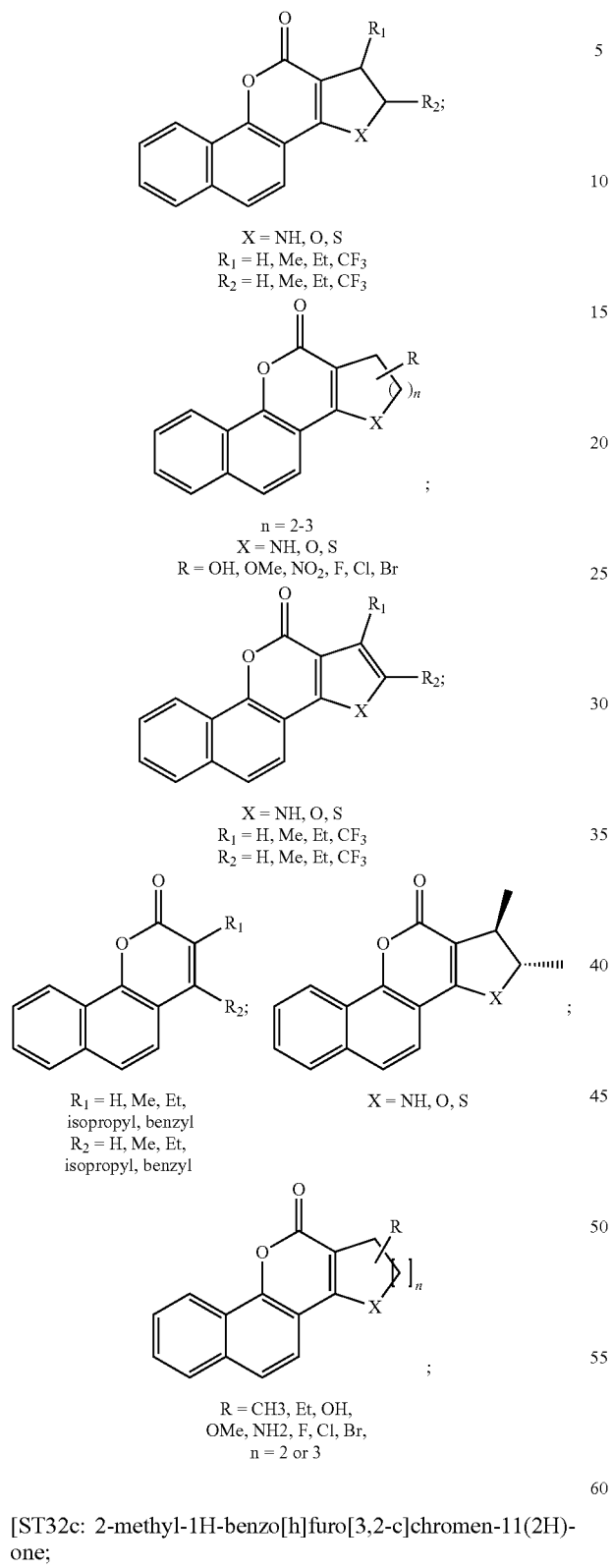

[ST32c: 2-methyl-1H-benzo[h]furo[3,2-c]chromen-11(2H)-one;
ST32da: (1R,2S)-1,2-dimethyl-1H-benzo[h]furo[3,2-c]chromen-11(2H)-one;
ST32db: (1R,2R)-1,2-dimethyl-1H-benzo[h]furo[3,2-c]chromen-11(2H)-one];

or a tautomer, enantiomer, stereoisomer thereof, or a solvate, prodrug or a pharmaceutically acceptable salt thereof.

In some other embodiments, the compound of Formula (I) is selected from the group consisting of:

(1) Substituted on A ring:

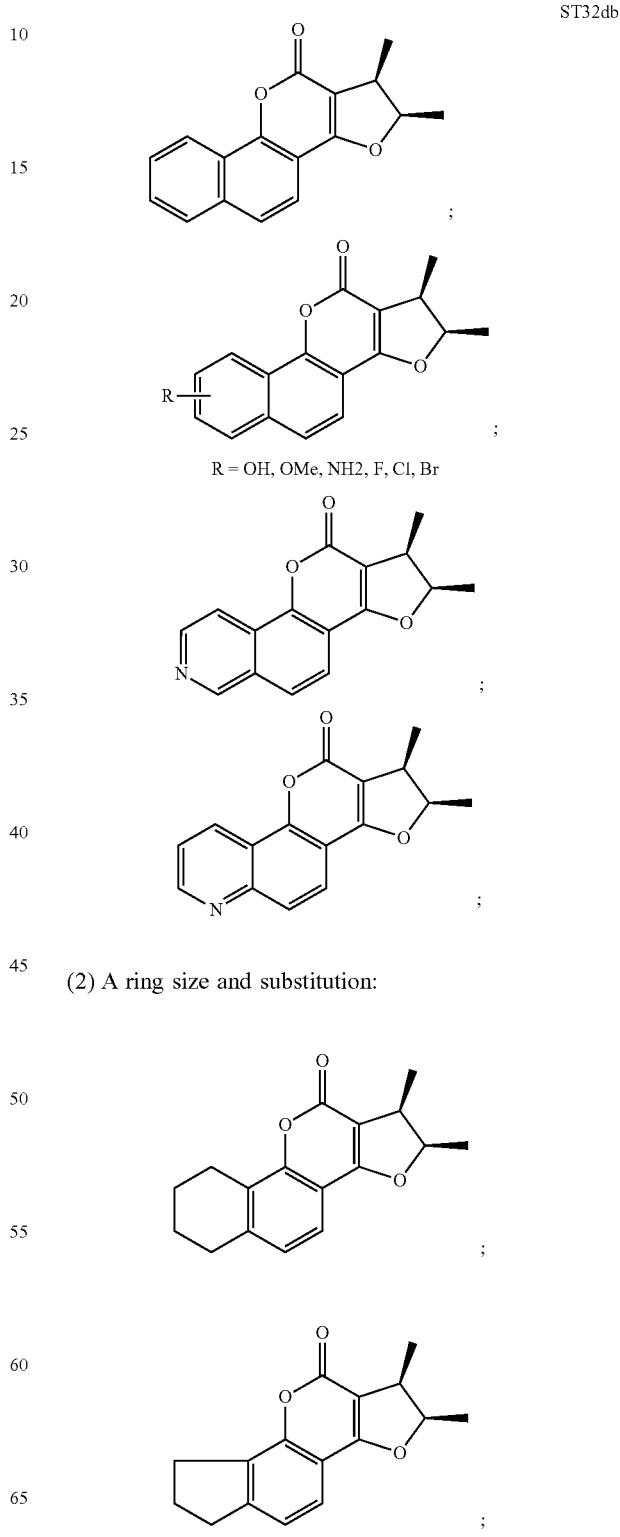

(2) A ring size and substitution:

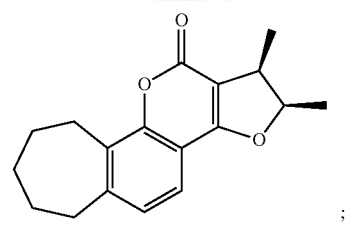
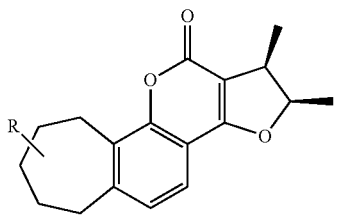
R = OH, OMe, NH2, F, Cl, Br ;
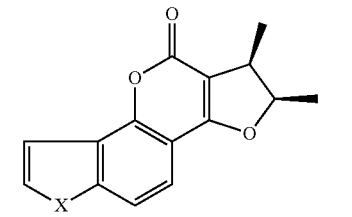
X = NH, O, S ;
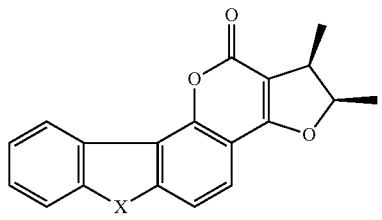
X = NH, O, S ;
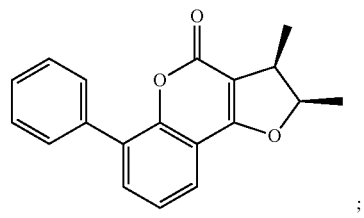
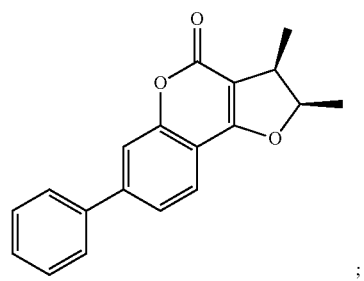
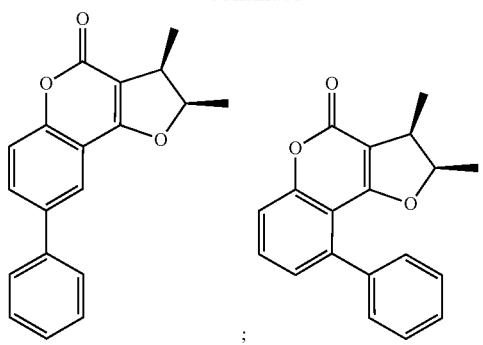
(3) B ring size and substitution:
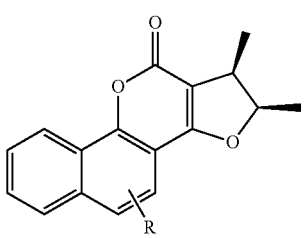
R = OH, OMe, NH2, F, Cl, Br
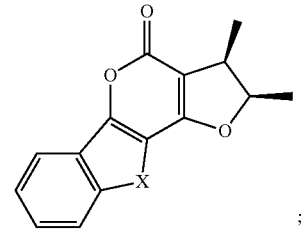
X = NH, O, S
(4) D ring size and substitution:
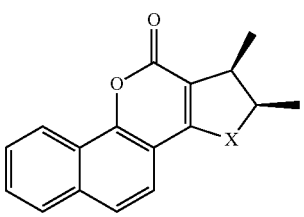
R = NH, O, S
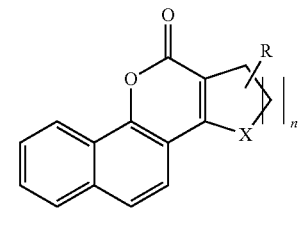
R = CH3, Et, OH, OMe, NH2, F, Cl, Br,

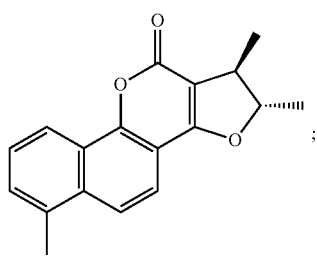

dihydrotanshinlactone

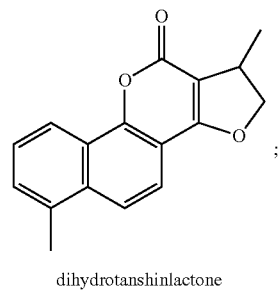

Salviatrinone-N

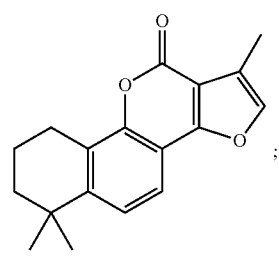

ST64

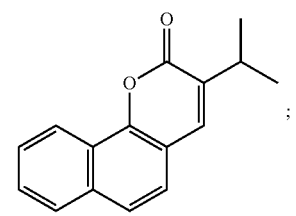

ST74

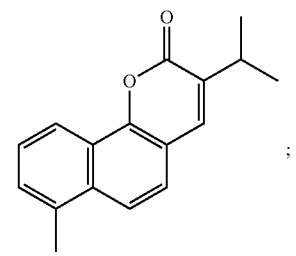

Salviatrinone-M

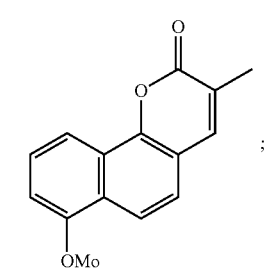

SM102

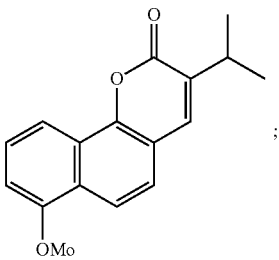

SM104

[ST32BA: (1R,2S)-1,2,6-trimethyl-1,2-dihydro-11H-benzo[h]furo[3,2-c]chromen-11-one;
WTS08: 1,6-dimethyl-1,2-dihydro-11H-benzo[h]furo[3,2-c]chromen-11-one;
WTS16: 1,6,6-trimethyl-6,7,8,9-tetrahydro-11H-benzo[h]furo[3,2-c]chromen-11-one;
ST64: 3-isopropyl-2H-benzo[h]chromen-2-one;
ST74: 3-isopropyl-7-methyl-2H-benzo[h]chromen-2-one;
SM102: 7-methoxy-3-methyl-2H-benzo[h]chromen-2-one;
SM104: 3-isopropyl-7-methoxy-2H-benzo[h]chromen-2-one];
or a tautomer, enantiomer, stereoisomer thereof, or a solvate, prodrug or a pharmaceutically acceptable salt thereof.

In some embodiments, the compound of Formula (I) is selected from the group consisting of:

ST32c: 2-methyl-1H-benzo[h]furo[3,2-c]chromen-11(2H)-one;
ST32da: (1R,2S)-1,2-dimethyl-1H-benzo[h]furo[3,2-c]chromen-11(2H)-one;
ST32da': (1R,2R)-5-chloro-1,2-dimethyl-1,2-dihydro-11H-benzo[h]furo[3,2-c]chromen-11-one;
ST32db: (1R,2R)-1,2-dimethyl-1H-benzo[h]furo[3,2-c]chromen-11(2H)-one;
ST32BA: (1R,2S)-1,2,6-trimethyl-1,2-dihydro-11H-benzo[h]furo[3,2-c]chromen-11-one;
WTS08: 1,6-dimethyl-1,2-dihydro-11H-benzo[h]furo[3,2-c]chromen-11-one;
WTS16: 1,6,6-trimethyl-6,7,8,9-tetrahydro-11H-benzo[h]furo[3,2-c]chromen-11-one;
ST64: 3-isopropyl-2H-benzo[h]chromen-2-one;
ST74: 3-isopropyl-7-methyl-2H-benzo[h]chromen-2-one;
SM102: 7-methoxy-3-methyl-2H-benzo[h]chromen-2-one;
SM104: 3-isopropyl-7-methoxy-2H-benzo[h]chromen-2-one;
6c: (1R,2S)-5-bromo-1,2-dimethyl-1,2-dihydro-11H-benzo[h]furo[3,2-c]chromen-11-one;
6c': (1R,2R)-5-bromo-1,2-dimethyl-1,2-dihydro-11H-benzo[h]furo[3,2-c]chromen-11-one;
10: (2S,3R)-2,3-dimethyl-6-phenyl-2,3-dihydro-4H-furo[3,2-c]chromen-4-one;
10': (2R,3R)-2,3-dimethyl-6-phenyl-2,3-dihydro-4H-furo[3,2-c]chromen-4-one;
11: (1R,2S)-1,2-dimethyl-1,2-dihydro-11H-benzo[h]furo[3,2-c]chromen-11-thione; and
11': (1R,2R)-1,2-dimethyl-1,2-dihydro-11H-benzo[h]furo[3,2-c]chromen-11-thione;
or a tautomer, enantiomer, stereoisomer thereof, or a solvate, prodrug or a pharmaceutically acceptable salt thereof.

The invention disclosed herein also encompasses prodrugs of the disclosed compounds. Prodrugs are considered to be any covalently bonded carriers that release an active compound of Formula (I) in vivo. Non-limiting examples of prodrugs include esters of compounds of Formula (I), and these may be prepared by reacting such compounds with anhydrides such as succinic anhydride.

The invention disclosed herein also encompasses pharmaceutically acceptable salts of the disclosed compounds. In one embodiment, the present invention includes any and all non-toxic, pharmaceutically acceptable salts of the disclosed compounds, comprising inorganic and organic acid addition salts and basic salts. The pharmaceutically acceptable salts of the present invention can be synthesized from the parent compound which contains a basic or acidic moiety by conventional chemical methods. Generally, such salts can be prepared by reacting the free acid or base forms of these compounds with a sufficient amount of the appropriate base or acid in water or in an organic diluent like ether, ethyl acetate, ethanol, isopropanol, or acetonitrile, or a mixture thereof. For example, such salts include acetates, ascorbates, benzenesulfonates, benzoates, besylates, bicarbonates, bitartrates, bromides/hydrobromides, Ca-edetates/edetates, camsylates, carbonates, chlorides/hydrochlorides, citrates, edisylates, ethane di sulfonates, estolates esylates, fumarates, gluceptates, gluconates, glutamates, glycolates, glycollylarsnilates, hexylresorcinates, hydrabamines, hydroxymaleates, hydroxynaphthoates, iodides, isothionates, lactates, lactobionates, malates, maleates, mandelates, methanesulfonates, mesylates, methylbromides, methylnitrates, methylsulfates, mucates, napsylates, nitrates, oxalates, pamoates, pantothenates, phenylacetates, phosphates/diphosphates, polygalacturonates, propionates, salicylates, stearates subacetates, succinates, sulfamides, sulfates, tannates, tartrates, teoclates, toluenesulfonates, triethiodides, ammonium, benzathines, chloroprocaines, cholines, diethanolamines, ethylenediamines, meglumines and procaines. Further pharmaceutically acceptable salts can be formed with cations from metals like aluminium, calcium, lithium, magnesium, potassium, sodium, zinc and the like. (See Pharmaceutical salts, Birge, S. M. et al., J. Pharm. Sci., (1977), 66, 1-19.)

The invention disclosed herein also encompasses solvates of the disclosed compounds. One type of solvate is a hydrate. Solvates typically do not contribute significantly to the physiological activity or toxicity of the compounds and as such can function as pharmacological equivalents.

The invention disclosed herein also encompasses tautomers and isomers of the disclosed compounds. A given chemical formula or name shall encompass tautomers and all stereo, optical and geometrical isomers (e.g. enantiomers, diastereomers, E/Z isomers etc.) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof and solvates thereof such as, for instance, hydrates including solvates of the free compounds or solvates of a salt of the compound.

Synthesis

Section 1

Scheme 1: Synthetic route to desired compounds 6 and 6'.

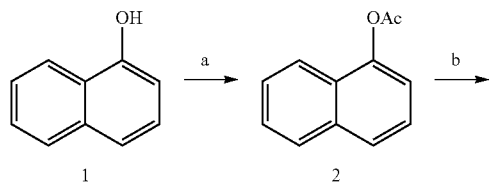

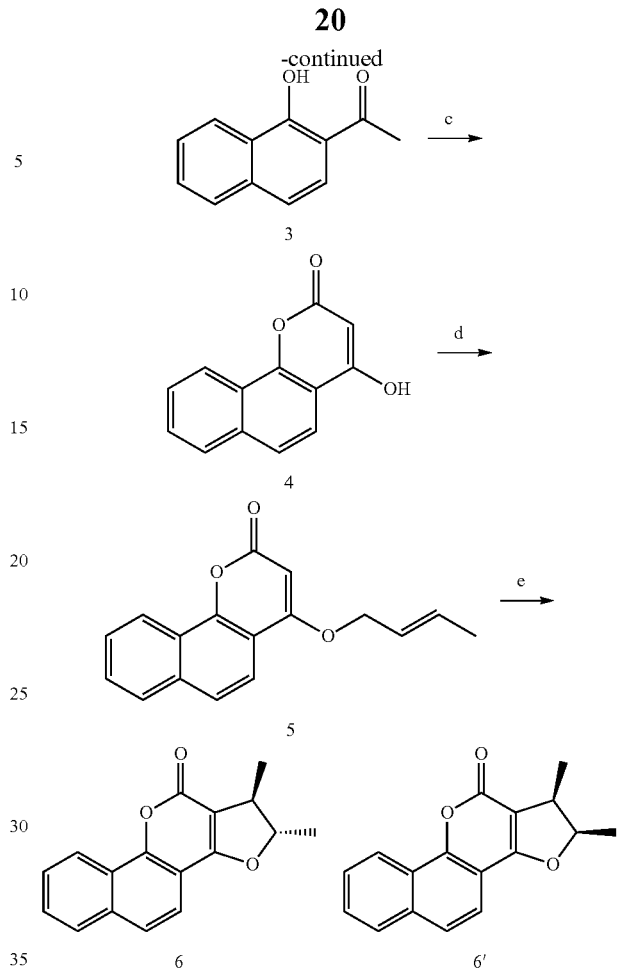

Reagents and conditions: a) acetic anhydride, DMAP, pyridine, reflux; b) AlCl₃, 135° C.; c) diethyl carbonate, NaH, toluene, 120° C.; d) crotyl bromide, K₂CO₃, acetone, 60° C.; e) BF₃—Et₂O, DMF, 140° C., M.W..

Synthesis of naphthalen-5-yl acetate (2)

The mixture of 1-naphthol (1) (1 g, 6.94 mmol), acetic anhydride (2.04 mL, 21.60 mmol), pyridine (0.026 mL, 0.31 mmol) and DMAP (84 mg, 0.69 mmol) was heated at 140° C. for 1.5 hr. After the reaction, the solution was diluted with EtOAc (50 mL), washed with distd H₂O (3×30 mL) and NaHCO₃ (3×30 mL), dried (Na₂SO₄), filtered and concentrated in vscuo. The residue was purified by flash chromatography (silica gel; EtOAc/n-hexane, 1:10) to give 2 (1.28 g, 99% yield) as yellow solid. ¹H NMR (300 MHz, CDCl₃): δ 7.91 (m, 2H), 7.79 (d, J=8.2 Hz, 1H), 7.55 (m, 3H), 7.29 (dd, J=1.0, 7.5 Hz, 1H), 2.52 (s, 3H).

Synthesis of 1-(1-hydroxynaphthalen-2-yl)ethanone (3)

The mixture of 2 (1 g, 5.37 mmol) and aluminum trichloride (1.15 g, 8.59 mmol) was heated at 135° C. for 0.5 hr. After the reaction, ice-water was added to the black residue. The solution was diluted with EtOAc (50 mL), washed with distd H₂O (3×30 mL), dried (Na₂SO₄), filtered and concentrated in vscuo. The residue was purified by flash chromatography (silica gel; EtOAc/n-hexane, 1:8) to give 3 (749 mg, 75% yield) as yellow solid. ¹H NMR (300 MHz, CDCl₃): δ 14.06 (s, 1H), 8.50 (d, J=9.1 Hz, 1H), 7.79 (d, J=5.1 Hz, 1H), 7.67 (m, 2H), 7.57 (m, 1H), 7.30 (d, J=8.9 Hz, 1H), 2.73 (s, 3H).

Synthesis of 4-hydroxy-2H-benzo[h]chromene-2-one (4)

To solution of 3 (700 mg, 3.76 mmol) in anhydrous toluene (15 mL) in ice-bath was slowly added NaH (903 mg, 37.63 mmol). Diethyl carbonate (0.68 mL, 5.65 mmol) in anhydrous toluene (3 mL) was added dropwise when hydrogen evolution was ceased. The mixture was stirred at 110° C. overnight. After reaction, the mixture was slowly added to ice-cold water (30 mL), then acidified with 2N HCl until precipitate was formed. The solid was filtered and collected to give 4 (614 mg, 77% yield) as yellow solid. $^1$H NMR (300 MHz, CDCl$_3$): δ 12.73 (br, 1H), 8.35 (m, 1H), 8.05 (m, 1H), 7.83 (s, 2H), 7.72 (m, 2H), 5.71 (s, 1H).

Section 2

Scheme 2: Synthesis of crotyl bromide

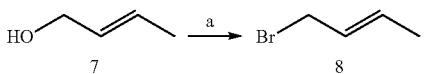

Reagents and conditions:
a) PBr$_3$, dry ether.

Synthesis of Crotyl Bromide (8)

To a solution of crotyl alcohol (7) (28.84 g, 400 mmol) in dry ether (100 mL) was added PBr$_3$ (18.8 mL, 200 mmol) via a syringe at 0° C. The mixture was stirred for 30 min at 0° C. and for additional 30 min at room temperature. Ice was added to quench the reaction. The ether layer was washed with brine, dried over MgSO$_4$ and evaporated to 30 mL to afforded 8 as a colorless oil. $^1$H NMR (400 MHz, CDCl$_3$): □δ 5.78 (m, 2H), 3.95 (d, J=7.2 Hz, 1H), 1.75 (d, J=6.2 Hz, 4H).

Synthesis of 4-hydroxy-2H-benzo[h]chromen-2-one (4)

The mixtures of 1-naphthol (1) (10 g, 69.44 mmol), malonic acid (7.22 g, 69.44 mmol), and PPA (100 g) was heated at 75° C. for 3 h. After the reaction, ice-water was added to the black residue. The solid was filtered, dissolved in 10% Na$_2$CO$_3$ solution, and stirred overnight. The basic solution was filtered, and the filtrate was acidified with 2 N HCl solution until the pH was about 4. The precipitate was then filtrated and purified by silica gel chromatography to yield 4 (5.89 g, 40%) as a brown solid. $^1$H NMR (400 MHz, CDCl$_3$): δ 8.35 (m, 1H), 8.04 (m, 1H), 7.83 (s, 1H), 7.72 (m, 2H), 5.70 (s, 1H).

Synthesis of (E)-4-(but-2-en-1-yloxy)-2H-benzo[h]chromen-2-one (5)

A solution of 4 (5.89 g, 27.78 mmol) and potassium carbonate (7.67 g, 55.56 mmol) in DMF (40 mL) was treated with crotyl bromide (8.5 mL, 83.34 mmol) and stirred under N$_2$ at 56° C. for 3 h. After filtration to remove K$_2$CO$_3$, the filtrate was concentrated in vacuo. The residue was diluted with EtOAc (50 mL), washed with distd H$_2$O (3×30 mL), dried (Na$_2$SO$_4$), filtered and concentrated in vscuo. The residue was purified by flash chromatography (silica gel; EtOAc/n-hexane, 1:7) to give 5 (3.03 g, 41% yield) as yellow solid. $^1$H NMR (400 MHz, CDCl$_3$): δ 8.57 (m, 1H), 7.89 (m, 1H), 7.85 (dd, J=2.7, 8.7 Hz, 1H), 7.67 (m, 3H), 5.98 (m, 1H), 5.83 (m, 1H), 5.80 (s, 1H), 4.83 (d, J=6.4 Hz, 0.7H), 4.68 (d, J=6.2 Hz, 1.3H), 1.82 (d, J=6.4 Hz, 3H).

Synthesis of (1R,2S)-1,2-dimethyl-1,2-dihydro-11H-benzo[h]furo[3,2-c]chromen-11-one (ST32da) and (1R,2R)-1,2-dimethyl-1,2-dihydro-11H-benzo[h]furo[3,2-c]chromen-11-one (ST32db)

To a solution of 5 (3.03 g, 11.39 mmol) in DMF (30 mL) was treated with 12 (1.50 g, 5.91 mmol). The resulting mixture was stirred under N$_2$ at 140° C. for 30 min then cooled to room temperature. The mixture was diluted with EtOAc (50 mL), washed with distd H$_2$O (3 □□30 mL), dried (Na$_2$SO$_4$), filtered and concentrated in vscuo. The residue was purified by flash chromatography (silica gel; EtOAc/n-hexane, 1:10) to give ST32da (757 mg, 25% yield) and ST32db (1.51 g, 50% yield) as light yellow solid. ST32da: $^1$H NMR (400 MHz, CDCl$_3$): δ 8.49 (m, 1H), 7.79 (m, 1H), 7.55 (m, 4H), 4.71(quintet, J=6.2, 12.68 Hz, 1H), 3.19 (quintet, J=6.6, 13.3 Hz, 1H), 1.55 (d, J=6.3 Hz, 3H), 1.43 (d, J=6.7 Hz, 3H). $^{13}$C NMR (100 MHz, CDCl$_3$): δ 166.7, 160.5, 152.6, 135.0, 128.6, 127.9, 127.0, 123.8, 123.0, 122.8, 118.2, 107.9, 105.7, 91.3, 42.2, 20.8, 18.0. HRMS (APCI) calcd for C$_{17}$H$_{14}$O$_3$ [M+H]$^+$: 266.0943; found: 267.1022. ST32db: $^1$H NMR (400 MHz, CDCl$_3$): δ 8.59 (m, 1H), 7.87 (m, 1H), 7.65 (m, 4H), 5.25 (quintet, J=6.8, 14.2 Hz, 1H), 3.60 (quintet, J=7.2, 14.8 Hz, 1H), 1.58 (d, J=6.7 Hz), 1.31 (d, J=7.1 Hz, 3H). $^{13}$C NMR(100 MHz, CDCl$_3$): δ 166.8, 160.6, 152.6, 135.1, 128.7, 127.9, 127.1, 123.9, 123.1, 122.9, 118.4, 107.9, 107.1, 86.8, 37.3, 15.3, 12.9. HRMS (APCI) calcd for C$_{17}$H$_{14}$O$_3$ [M+H]$^+$: 266.0943; found: 267.1014.

Synthesis of (1R,2S)-5-methoxy-1,2-dimethyl-1,2-dihydro-11H-benzo[h]furo[3,2-c]chromen-11-one (6a) and (1R,2R)-5-methoxy-1,2-dimethyl-1,2-dihydro-11H-benzo[h]furo[3,2-c]chromen-1 1-one (6a')

Following the procedure as ST32da to give 6a (42 mg, 27% yield) and 6a' (80 mg, 52% yield) as light yellow solid. 6a: $^1$H NMR (400 MHz, CDCl$_3$): δ 8.52 (m, 1H), 8.26 (m, 1H), 7.64 (m, 2H), 6.82 (s, 1H), 4.75 (quintet, J=6.0, 12.4 Hz, 1H), 4.04 (s, 3H), 3.23 (quintet, J=6.8, 13.2 Hz, 1H), 1.58 (d, J=6.4 Hz, 3H), 1.46 (d, J=6.8 Hz, 3H). $^{13}$C NMR (100 MHz, CDCl$_3$): δ 166.6, 160.8, 151.8, 147.4, 128.1, 127.5, 124.0, 122.6, 122.3, 107.6, 106.0, 94.5, 91.3, 55.8, 42.3, 20.8, 18.1. HRMS (FAB) calcd for C$_{18}$H$_{17}$O$_4$ [M+H]$^+$: 297.1127; found: 297.1121. 6a': $^1$H NMR (400 MHz, CDCl$_3$): δ 8.52 (m, 1H), 8.26 (m, 1H), 7.64 (m, 2H), 6.79 (s, 1H), 5.22 (quintet, J=6.8, 13.5 Hz, 1H), 4.02 (s, 3H), 3.57 (quintet, J=7.2, 14.1 Hz, 1H), 1.57 (d, J=6.8 Hz, 3H), 1.29 (d, J=7.2 Hz, 3H). $^{13}$C NMR (100 MHz, CDCl$_3$): δ 166.6, 160.7, 151.7, 147.2, 128.1, 127.6, 127.5, 123.9, 122.6, 122.3, 107.4, 107.2, 94.5, 86.7, 55.8, 37.4, 15.3, 12.8. FIRMS (FAB) calcd for C$_{18}$H$_{17}$O$_4$ [M+H]$^+$: 297.1127; found: 297.1121.

Synthesis of (1R,2S)-5-chloro-1,2-dimethyl-1,2-dihydro-11H-benzo[h]furo[3,2-c]chromen-11-one (6b) and (1R,2R)-5-chloro-1,2-dimethyl-1,2-dihydro-11H-benzo[h]furo[3,2-c]chromen-11-one (6b')

Following the procedure as ST32da to give 6b (73 mg, 24% yield) and 6b' (167 mg, 55% yield) as light yellow solid. 6b: $^1$H NMR (400 MHz, CDCl$_3$): δ 8.59 (d, J=8.2 Hz, 1H), 8.27 (d, J=8.3 Hz, 1H), 7.73 (m, 3H), 4.73 (quintet, J=6.4, 12.8 Hz, 1H), 3.24 (quintet, J=6.4, 13.2 Hz, 1H), 1.59 (d, J=6.4 Hz, 3H), 1.46 (d, J=6.8 Hz, 3H). $^{13}$C NMR (100 MHz, CDCl$_3$): δ 165.7, 160.0, 151.4, 132.0, 129.5, 127.8, 127.4, 124.8, 124.1, 123.3, 118.2, 108.0, 106.4, 91.6, 42.2, 20.7, 17.9. HRMS (EI) calcd for C$_{17}$H$_{13}$ClO$_3$ [M]$^+$: 300.0553; found: 300.0552. 6b': H NMR (400 MHz, CDCl$_3$): δ 8.59 (d, J=8.0 Hz, 1H), 8.27 (d, J=8.2 Hz, 1H), 7.73 (m, 3H), 5.27 (quintet, J=6.8, 13.2 Hz, 1H), 3.60 (quintet, J=7.2, 14.4 Hz, 1H), 1.58 (d, J=6.8 Hz, 3H), 1.31 (d, J=7.2 Hz, 3H). $^{13}$C NMR (100 MHz, CDCl$_3$): δ 165.8, 160.0, 151.3, 132.0, 129.5, 127.8, 127.4, 124.8, 124.1, 123.3, 118.2, 107.9, 107.6, 87.1, 37.4, 15.2, 12.7. HRMS (EI) calcd for C$_{17}$H$_{13}$ClO$_3$ [M]$^+$: 300.0553; found: 300.0052.

Synthesis of (1R,2S)-5-bromo-1,2-dimethyl-1,2-dihydro-11H-benzo[h]furo[3,2-c]chromen-11-one (6c) and (1R,2R)-5-bromo-1,2-dimethyl-1,2-dihydro-11H-benzo[h]furo[3,2-c]chromen-11-one (6c')

Following the procedure as ST32da to give 6c (64 mg, 26% yield) and 6c' (120 m g, 49% yield) as light yellow solid. 6c: $^1$H NMR (400 MHz, CDCl$_3$): δ 8.57 (d, J=8.0 Hz, 1H), 8.23 (d, J=8.3 Hz, 1H), 7.92 (s, 1H), 7.73 (m, 2H), 4.78 (quintet, J=6.4, 12.8 Hz, 1H), 3.24 (quintet, J=6.8, 13.6 Hz, 1H), 1.59 (d, J=6.4 Hz, 3H), 1.46 (d, J=6.4 Hz, 3H). $^{13}$C NMR (100 MHz, CDCl$_3$): δ 165.6, 160.0, 152.0, 133.1, 129.8, 127.8, 127.4, 124.1, 123.2, 121.9, 117.5, 108.5, 106.4, 91.6, 42.2, 20.7, 17.9. HRMS (EI) calcd for C$_{17}$H$_{13}$BrO$_3$ [M]$^+$: 344.0048; found: 344.0046. 6c': $^1$H NMR (400 MHz, CDCl$_3$): δ 8.58 (d, J=8.3 Hz, 1H), 8.24 (d, J=8.3 Hz, 1H), 7.93 (s, 1H), 7.73 (m, 2H), 5.27 (quintet, J=6.8, 13.2 Hz, 1H), 3.60 (quintet, J=7.2, 14.4 Hz, 1H), 1.58 (d, J=6.8 Hz, 3H), 1.31 (d, J=7.2 Hz, 3H). $^{13}$C NMR (100 MHz, CDCl$_3$): δ 165.6, 159.9, 151.9, 133.1, 129.8, 127.8, 127.5, 124.2, 123.2, 121.9, 117.6, 108.4, 107.6, 87.1, 37.3, 15.2, 12.7. HRMS (EI) calcd for C$_{17}$H$_{13}$BrO$_3$ [M]$^+$: 344.0048; found: 344.0041.

Synthesis of (2S,3R)-2,3-dimethyl-6-phenyl-2,3-dihydro-4H-furo[3,2-c]chromen-4-one (10) and (2R,3R)-2,3-dimethyl-6-phenyl-2,3-dihydro-4H-furo[3,2-c]chromen-4-one (10')

Following the procedure as ST32da to give 10 (94 mg, 28% yield) and 10' (181 mg, 54% yield) as light yellow solid. 10: $^1$H NMR (400 MHz, CDCl$_3$): δ 7.64 (m, 4H), 7.48 (t, J=7.3 Hz, 2H), 7.41 (d, J=7.3 Hz, 1H), 7.34 (t, J=7.7 Hz, 1H), 5.21 (quintet, J=6.8, 13.6 Hz, 1H), 3.54 (quintet, J=7.2, 14.4 Hz, 1H), 1.56 (d, J=6.8 Hz, 3H), 1.27 (d, J=7.2 Hz, 3H). $^{13}$C NMR (100 MHz, CDCl$_3$): δ 165.9, 160.2, 151.8, 136.1, 133.3, 130.3, 129.5, 128.4, 127.9, 123.7, 121.9, 113.2, 107.6, 86.7, 37.4, 15.2, 12.8. HRMS (FAB) calcd for C$_{19}$H$_{17}$O$_3$ [M+H]$^+$: 293.1178; found: 293.1172. 10': $^1$H NMR (400 MHz, CDCl$_3$): δ 7.64 (m, 4H), 7.49 (t, J=7.4 Hz, 2H), 7.42 (d, J=7.3 Hz, 1H), 7.35 (t, J=7.7 Hz, 1H), 4.75 (quintet, J=6.4, 12.8 Hz, 1H), 3.19 (quintet, J=6.4, 13.2 Hz, 1H), 1.56 (d, J=6.4 Hz, 3H), 1.42 (d, J=6.8 Hz, 3H). $^{13}$C NMR (100 MHz, CDCl$_3$): δ 165.7, 160.2, 151.9, 136.1, 133.3, 130.3, 129.5, 128.4, 127.9, 123.7, 121.9, 113.3, 106.3, 91.2, 42.3, 20.8, 18.1. HRMS (FAB) calcd for C$_{19}$H$_{17}$O$_3$ [M]$^+$: 293.1178; found: 293.1184.

Synthesis of (1R,2S)-1,2-dimethyl-1,2-dihydro-11H-benzo[h]furo[3,2-c]chromen-11-thione (11) and (1R,2R)-1,2-dimethyl-1,2-dihydro-11H-benzo[h]furo[3,2-c]chromen-11-thione (11')

A mixture of compound 32da or 32db (50 mg, 0.18 mmol) and Lawesson's reagent (145 mg, 0.36 mmol) in dry toluene (5 mL) was heated to reflux for 1 h. The mixture was diluted with EtOAc (50 mL), washed with distd H$_2$O (3×30 mL), dried (Na$_2$SO$_4$), filtered and concentrated in vscuo. The residue was purified by flash chromatography (silica gel; EtOAc/n-hexane, 1:10) to give 11 (44 mg, 87% yield) and 11' (45 mg, 89% yield) as light yellow solid. 11: $^1$H NMR (400 MHz, CDCl$_3$): δ 8.74 (d, J=8.7 Hz, 1H), 7.89 (d, J=6.9 Hz, 1H), 7.70 (m, 4H), 4.85 (quintet, J=6.2, 12.2 Hz, 1H), 3.31 (quintet, J=6.5, 13.0 Hz, 1H), 1.57 (d, J=6.6 Hz, 6H). $^{13}$C NMR (100 MHz, CDCl$_3$): δ 191.9, 161.9, 135.1, 129.5, 127.9, 127.5, 125.3, 123.3, 123.0, 122.5, 118.0, 109.5, 92.1, 43.9, 20.9, 17.1. HRMS (EI) calcd for C$_{17}$H$_{14}$O$_2$S [M]$^+$: 282.0715; found: 282.0718. 11': $^1$H NMR (400 MHz, CDCl$_3$): δ 8.71 (m, 1H), 7.86 (m, 1H), 7.67 (m, 4H), 5.25 (quintet, J=6.7, 13.6 Hz, 1H), 3.62 (quintet, J=7.2, 14.8 Hz, 1H), 1.62 (d, J=6.7 Hz, 3H), 1.40 (d, J=7.2 Hz, 3H). $^{13}$C NMR(100 MHz, CDCl$_3$): δ 191.6, 162.0, 156.8, 135.1, 129.5, 127.9, 127.5, 125.3, 124.8, 123.3, 122.5, 118.0, 109.3, 87.9, 39.5, 15.2, 11.3. HRMS (EI) calcd for C$_{17}$H$_{14}$O$_2$S [M]$^+$: 282.0715; found: 282.0707.

The invention uses a platform of ATF3 promoter luciferase to select AT3 inducer and confirms that these selected compounds can be used as anti-obesity, anti-diabetes and anti-heart disease drugs in view of the fact that these compounds have an inhibitory effect on obesity and obesity-induced diabetes and inhibition of high blood pressure or hypoxia induced cardiomyopathy, thereby increasing heart function. The platform of ATF3 promoter luciferase is created by transfecting a DNA sequence of ATF3 (pGL4-ATF3) into 3T3-L1 preadipocytes and H9C2 cardiomyocytes and using the stable clones as a platform for screening of drugs for anti-obesity, anti-atherosclerosis, anti-cardiovascular disease and promotion of white-to-brown adipocyte transdifferentiation.

Compositions and Applications

In another aspect, the invention provides a pharmaceutical composition comprising a compound of the invention and a pharmaceutically acceptable carrier.

The compound may be formulated into pharmaceutical compositions that may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Pharmaceutically acceptable carriers and diluents are familiar to those skilled in the art. For compositions formulated as liquid solutions, acceptable carriers and/or diluents include saline and sterile water, and may optionally include antioxidants, buffers, bacteriostats and other common additives. The compositions can also be formulated as pills, capsules, granules, or tablets which contain, in addition to a compound of the invention, diluents, dispersing and surface active agents, binders, and lubricants. One skilled in this art may further formulate the compound of the invention in an appropriate manner, and in accordance with accepted practices, such as those disclosed in Remington's Pharmaceutical Sciences, Gennaro, Ed., Mack Publishing Co., Easton, Pa. 1990.

In a preferred embodiment, the compound is present in the composition in an amount that is effective to achieve its intended therapeutic purpose. While individual needs may vary, a determination of optimal ranges of effective amounts of each compound is within the skill of the art.

The compounds of the present invention may be useful in combination with one or more second therapeutic agents, particularly therapeutic agents suitable for the treatment and/or prevention of the conditions and diseases presented herein.

In another aspect, the invention provides a method of selecting AT3 inducer as an anti-obesity agent, an anti-atherosclerosis agent or an anti-cardiovascular agent, comprising contacting a compound with a cell transfected with a recombinant ATF3, detecting ATF3 expression of the cell and determining whether the compound is an AT3 inducer when the cell expresses a protein transcribed from AT3. In one embodiemtn, ATF3 inducers can be selected in pGL4-ATF3 stable clones of 3T3-L1 preadipocytes. Selected ATF3 inducers will be confirmed by measurement of ATF3 expression in 3T3-L1 preadipocytes.

In another aspect, the invention provides a method for treating and/or preventing obesity, comprising administering an effective amount of the compound of the invention to a subject. In one embodiment, the method can prevent or treat HFD-induced obesity. In a further embodiment, the compound can treat and/or prevent obesity-induced diabetes, inhibit high blood pressure or hypoxia induced cardiomyopathy thereby increasing heart function. In a further embodiment, the compound of the invention is in an amount ranging from 1 mg/kg/day to 2,000 mg/kg/day.

Such method includes administering a compound of the present invention to a subject in an amount sufficient to treat the condition. The actual therapeutically effective amount or therapeutic dosage will of course depend on factors known by those skilled in the art such as age and weight of the patient, route of administration and severity of disease. In any case, the combination will be administered at dosages and in a manner which allow a therapeutically effective amount to be delivered based upon subject's unique condition.

For oral administration, suitable pharmaceutical compositions of the invention include powders, granules, pills, tablets, lozenges, chews, gels, and capsules as well as liquids, syrups, suspensions, elixirs, and emulsions. These compositions may also include anti-oxidants, flavorants, preservatives, suspending, thickening and emulsifying agents, colorants, flavoring agents and other pharmaceutically acceptable additives. Formulations for oral administration may be formulated to be immediate release or modified release, where modified release includes delayed, sustained, pulsed, controlled, targeted and programmed release.

For parenteral administration, the compounds of the present invention are administered directly into the blood stream, into muscle, or into an internal organ via an intravenous, intraarterial, intraperitoneal, intramuscular, subcutaneous or other injection or infusion. Parenteral formulations may be prepared in aqueous injection solutions which may contain, in addition to the compound of the invention, buffers, antioxidants, bacteriostats, salts, carbohydrates, and other additives commonly employed in such solutions. Parenteral administrations may be immediate release or modified release (such as an injected or implanted depot).

Compounds of the present invention may also be administered topically, (intra)dermally, or transdermally to the skin or mucosa. Typical formulations include gels, hydrogels, lotions, solutions, creams, ointments, dressings, foams, skin patches, wafers, implants and microemulsions. Compounds of the present invention may also be administered via inhalation or intranasal administration, such as with a dry powder, an aerosol spray or as drops. Additional routes of administration for compounds of the present invention include intravaginal and rectal (by means of a suppository, pessary or enema), ocular and aural.

Alternatively, the compound of the invention can be formulated with a food grade carrier excipient, diluent and/or salt as a food, health food or a dietary supplement. The above-mentioned carrier excipient, diluent and/or salt can be used in the food, health food or a dietary supplement of the invention. Food, health food or dietary supplements may exist in various forms, including, but not limited to tablets, capsules, caplets, powders, drinks including shakes, solid food items including snack bars, etc.

It will be readily apparent to one of ordinary skill in the relevant arts that other suitable modifications and adaptations to the methods and applications described herein can be made without departing from the scope of the invention or any embodiment thereof. The following examples are offered to illustrate but not limit the invention.

EXAMPLE

Materials and Methods

Echocardiography Studies

For echocardiography, mice were anesthetized with pentobarbital (40 mg/kg body weight, i.p.) and then measurements were taken with ultrasound equipment (ATL Philips IE33, Ultrasound Machine System, CA, U.S.A.) using a 15-MHz probe. The left ventricular posterior wall thickness (LVPW), inter-ventricular septum thickness (IVS), and left ventricular lumen diameter at both end-systolic and end-diastolic phases were measured digitally on the M-mode tracings and averaged for three cardiac cycles. Fractional shortening (FS) and ejection faction (EF) were then calculated.

Real-Time Quantitative PCR and Reverse Transcriptase (RT)-PCR

Total RNA was extracted from cultured cells or tissues with TRIzol (Invitrogen), and 1 ug total RNA was reverse transcribed to cDNA with iScript cDNASynthesis Kit (Bio-Rad), according to the manufacturers' instructions. The ABI PRISM 7700 Sequence Detection System (ABI) was used for real-time quantitative PCR analysis. For detection of relative adipogenic, lipogenic and lipolytic mRNA expression of C/EBPα, C/EBPβ, PPAR γ1, PPAR γ2, FABP4, adiponectin, leptin, Resistin, Perilipin1, Perilipin 2, ACC1, ACC2, FAS, DGAT1, DGAT2, SCD1, ChREBP, SREBP1, ATGL, HSL, and MGL were measured by specific 5' and 3' primer. Real-time PCR was conducted using SYBR Green enzyme detection and GAPDH as mRNA internal control.

Production of Recombinant Adeno-Associated Virus Carrying ATF3

Full-length ATF3 was obtained by PCR amplification from a human complementary cDNA library, flanking the XbaI and HindIII restriction cutting sites, and was cloned into the pAAV-MCS vector. To produce the AAV virus, a three-plasmid cotransfection method was used (Xiao et al., 1998). The plasmids used in transfection were as follows: 1) the AAV-CMV-ATF3 plasmid with the gene driven by the CMV promoter, which carried the promoter-driven transgene flanked by AAV inverted terminal repeats; 2) the helper plasmid, which contained helper genes from the adenovirus; and 3) the pseudotyped AAV packaging plasmid containing the AAV8 serotype capsid gene coupled with the AAV2 rep gene. The AAVGFP (control) or AAVATF3 (experimental group) was purified twice by caesium chloride gradient ultracentrifugation, and the titer of vector genome particles was determined using a previously described method (Rabinowitz et al., 2002). The recombinant viruses with $1 \times 10^{12}$ viral particles in 30 ul of PBS were injected into a mouse-tail vein 2 weeks after TAB treatment.

GTT and ITT Assays

To evaluate HFD-induced glucose intolerance and insulin resistance, we performed glucose tolerance tests (GTTs) and insulin tolerance tests (ITTs) after 12 wks of NCD (normal chow diet) or HFD feeding as previously demonstrated. Mice were fasted overnight for 16 h before receiving an intraperitoneal administration of 1.5 g glucose/kg body weight in saline. Blood samples were collected from the tail vein by tail snipping at 0, 15, 30, 45, 60, and 120 min, and plasma glucose and insulin levels were determined from those samples. An ITT was performed on mice after 1 h of fasting. Animals were intraperitoneally injected with 1.0 U insulin/kg body weight in saline. Blood samples were drawn from the tail vein at 0, 15, 30, 45 and 60 min for the measurement of plasma glucose levels. Plasma glucose levels in blood samples collected from tail veins were determined using a commercially available glucose meter (OneTouch Ultra blood glucose meter, LifeScan, Milpitas, Calif.). After the isolation of plasma from blood samples, insulin levels were determined by ELISA (Mercodia, Winston Salem, N.C.). To evaluate the degree of insulin resistance, values were calculated using the following homeostatic model of assessment of insulin resistance (HOMA-IR) formula: fasting glucose (in mg/dl)×fasting insulin (in mU/ml)/405.)

Animal Model for Obesity

Male mice (weighing 25-30 g at six weeks old) were fed with 45% high fat diet (HFD) and intraperitoneal injection of AAV-ATF3 virus or AAV-GFP as control. In other experiments, mice were treated with ST32c, ST32da, ST32db by intraperitoneal injection at dose of 0.5 mg/kg/day or 1 mg/kg/day.

Animal Model of Cardiac Transverse Aortic Banding

Male mice (weighing 25-30 g) were anesthetized by intraperitoneal injection of chloral hydrate (125 mg/kg). The TAB procedure was performed according to the description by Hu et al. (Hu P, Zhang D, Swenson L, Chakrabarti G, Abel E D, and Litwin S E (2003) Minimally invasive aortic banding in mice: effects of altered cardiomyocyte insulin signaling during pressure overload. Am J Physiol Heart Circ Physiol 285:H1261-H1269). Echocardiography was performed at week 10 after TAB or sham surgery.

Example 1

ATF3 Prevents Diet-Induced Obesity and Metabolic Dyshomeostasis

Figure 1B:
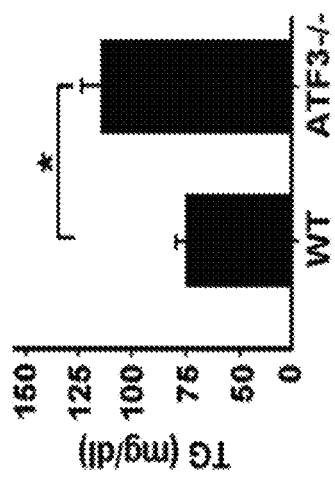
Figure 1C:
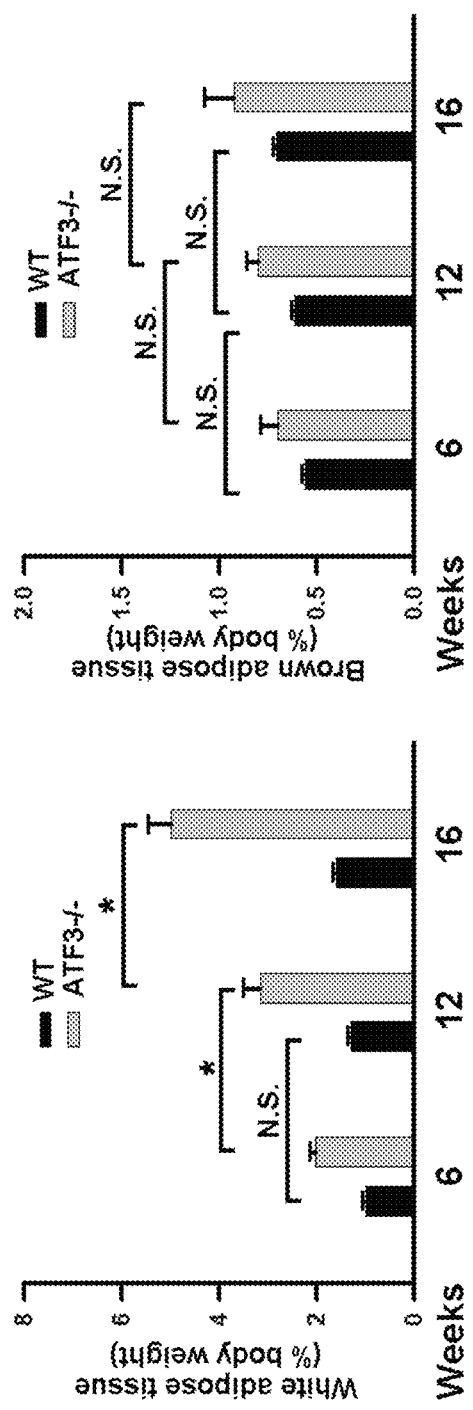
Figure 1D:
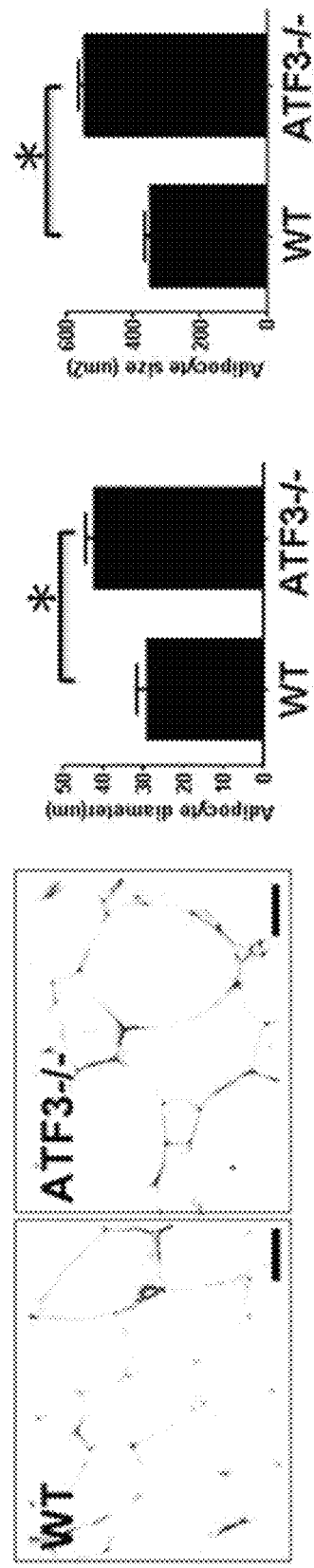
Figure 1E:
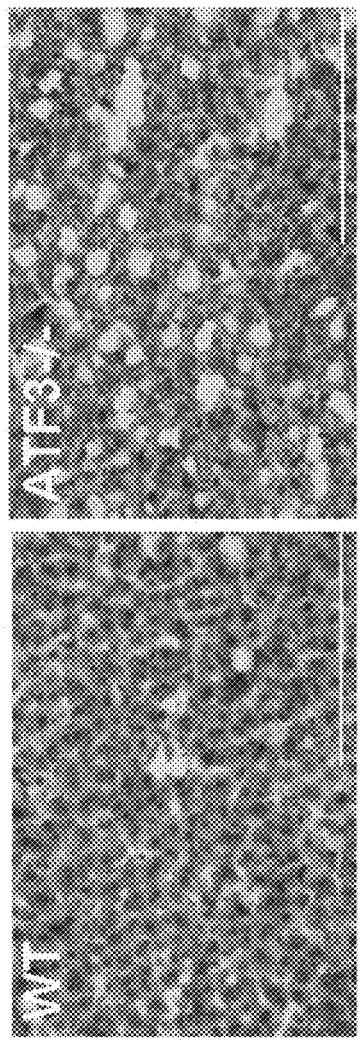

Mice were fed control or HFD for 12 or 16 weeks in the animal model for obesity. FIG. 1 shows that ATF3 prevents diet-induced obesity and metabolic dyshomeostasis. Here we demonstrated that ATF3 can regulate lipid metabolism in normal diet (ND) and high fat diet (HFD) in mice. ATF3−/− mice showed significantly increased body weight compared to WT mice after ND for 16 weeks (FIG. 1A, left panel). Furthermore, ATF3−/− mice showed significantly increased body weight compared to WT mice after HFD for 9 weeks (FIG. 1A, right panel). Elevated serum TG levels were observed in ATF3−/− mice as compared to WT mice (FIG. 1B). Further analysis for white adipose tissue (WAT) and brown adipose tissue (BAT), ATF3−/− mice exhibited significantly increased WAT mass compared to WT mice after 6, 12, 16 weeks of HFD (FIG. 1C, left panel), but no difference was shown in BAT mass between ATF3−/− mice and WT mice at after 6, 12, 16 weeks of HFD (FIG. 1C, right panel). We also performed HE staining and measured adipocyte sizes. The ATF3−/− mice had larger adipocyte diameter and size than the WT mice (FIG. 1D). ATF3−/− mice also showed hepatic lipid accumulation stained by Oil Red 0 stain as compared to WT mice (FIG. 1E).

Example 2

Figure 2B:
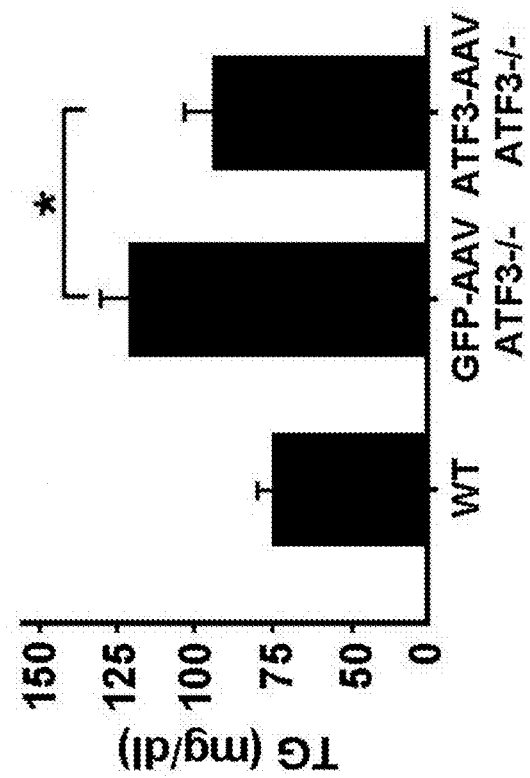
FIGS. 2 (A) to (D) show that adeno-associated virus-mediated expression of ATF3 reverses metabolic dyshomeostasis in ATF3−/− mice. (A) Body weight changes of wild-type (WT), GFP-AAV ATF3−/− and ATF3-AAV ATF3−/− mice fed a HFD, (n=8 per group). (B) Serum triglyceride level in wild-type (WT), GFP-AAV ATF3−/− and ATF3-AAV ATF3−/− mice fed a HFD. (C) Adipocyte diameter, size, number, and perigonadal fat pads weight per body weight. (D) Histology of epididymal WAT in wild-type (WT), GFP-AAV ATF3−/− and ATF3-AAV ATF3−/− mice after HFD for 8 weeks. Scale bar=100 (n=6 per group).
Figure 2A:
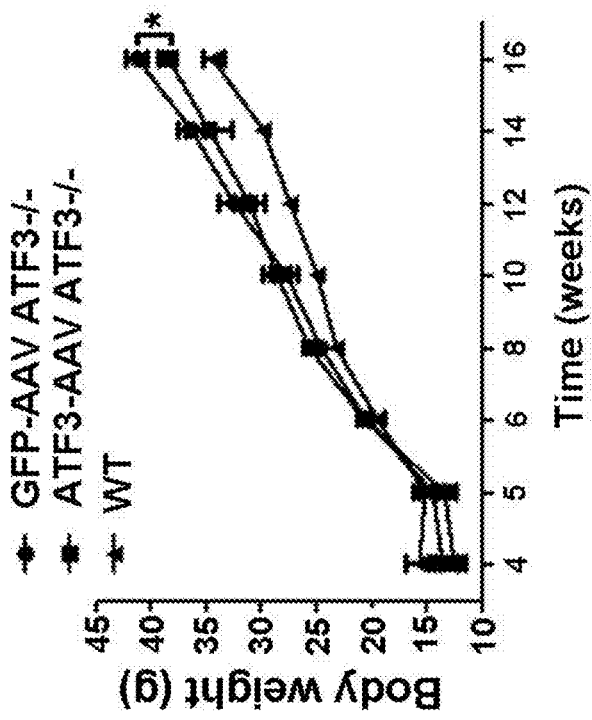
Figure 2C:
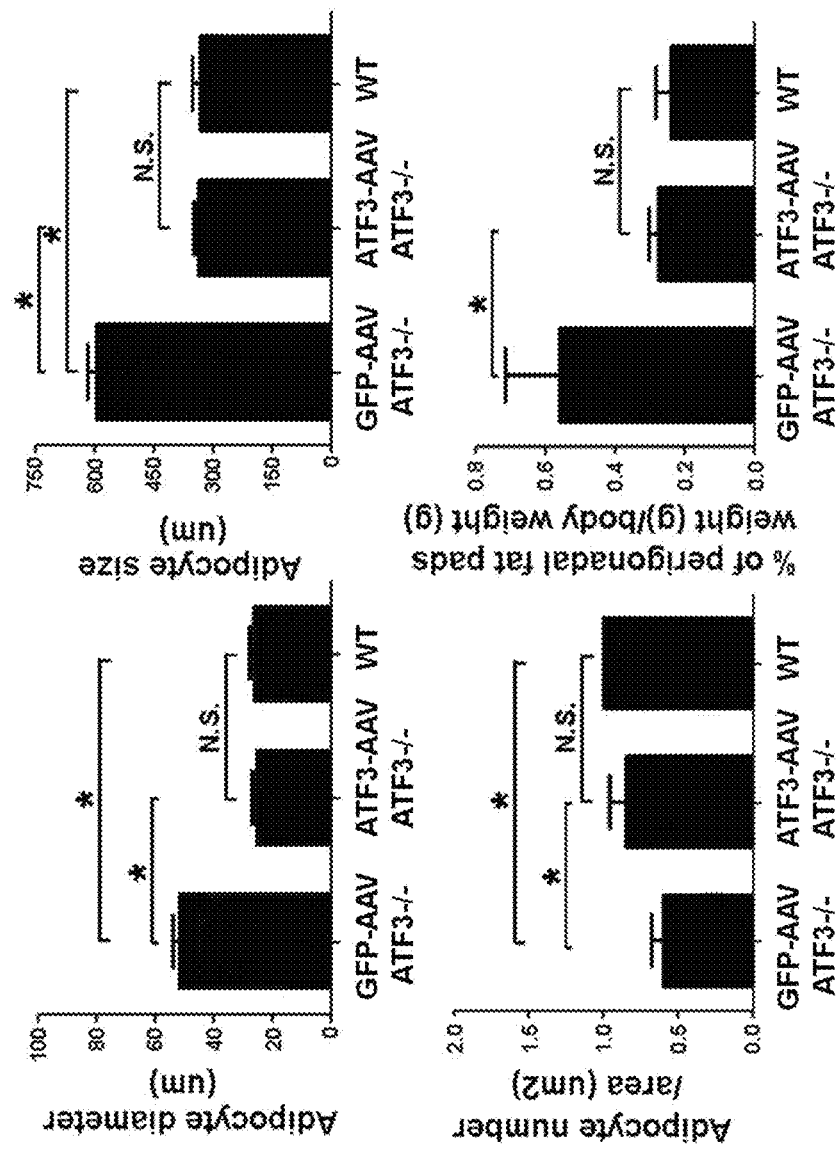
Figure 2D:
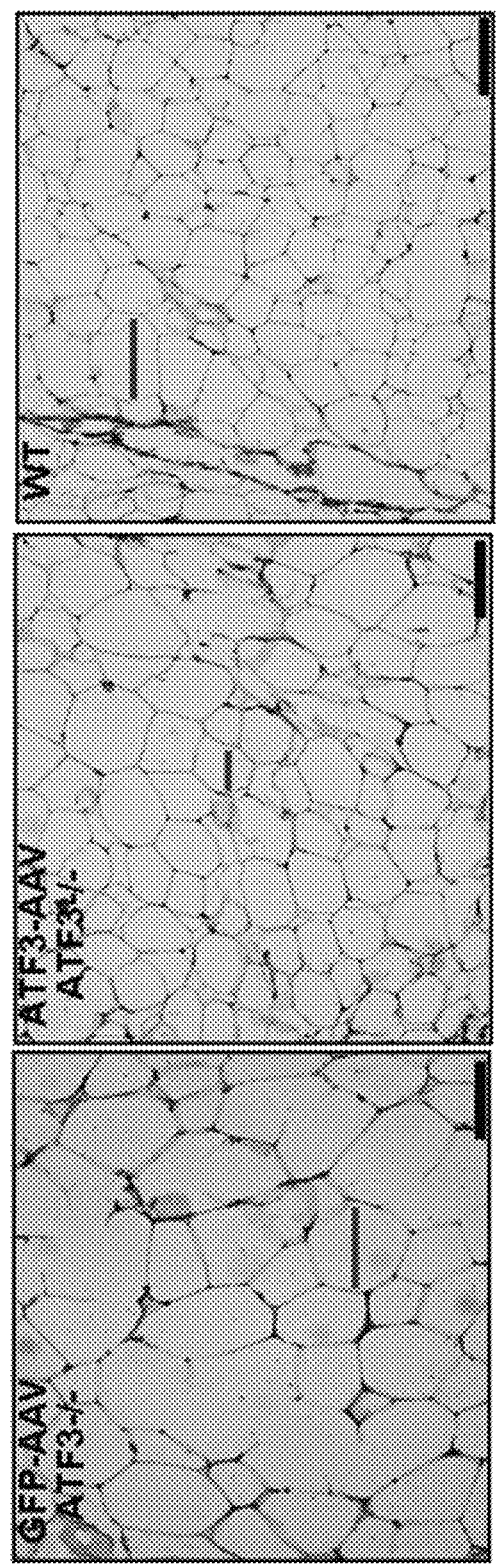

Restoration of ATF3 Expression in ATF3−/− Mice Reduces Obesity-Induced Metabolism Syndrome The obese ATF3−/− mice received AAV8-mediated gene transfer of ATF3 (AAV8-ATF3), in which decreased body weights were observed as compared to ATF3−/− mice receiving AAV8-GFP as control group after HFD for 16 weeks (AAV8-ATF3: 36.5±0.7 gm, p<0.05, n=6) (FIG. 2A). Elevated serum TG levels observed in ATF3−/−mice can be reversed by AAV8-ATF3 therapy (FIG. 2B). Histology demonstrated increased adipocyte diameter, size and number in ATF3−/− mice, in which such enlargement of adipocytes can be reversed by AAV8-ATF3 therapy. Increased perigonadal fat pad in ATF3−/− mice also can be reversed by AAV8-ATF3 therapy. (FIGS. 2C and 2D).

Example 3

ATF3 Prevents HFD-Induced Diabetes

Figure 3:
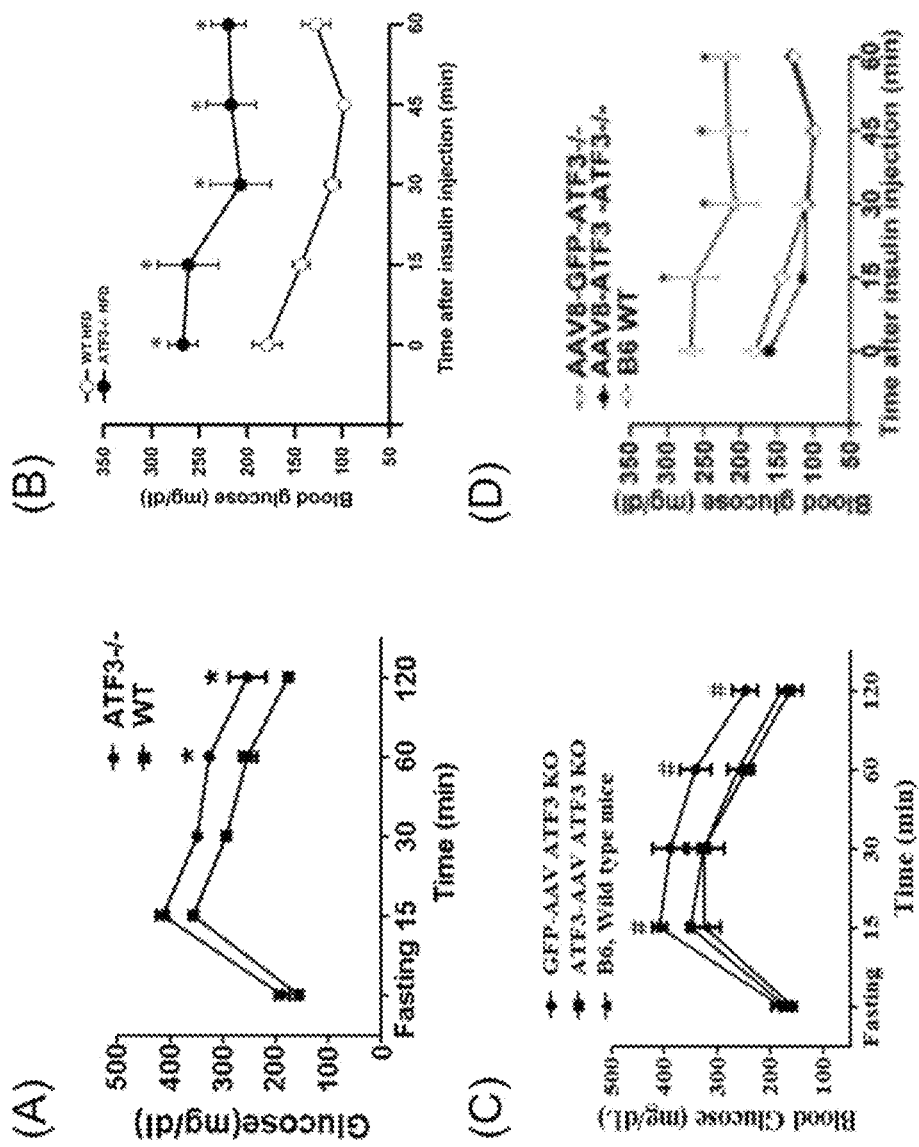
FIGS. 3 (A) to (D) show that ATF3 prevents diet-induced diabetis. Mice were fed a HFD for 12 weeks. (A) Glucose tolerance test. (B) Insulin tolerance test. (C) Glucose tolerance test and (D) insulin tolerance test of mice infused with AAV8-ATF3 or AAV8-GFP in ATF3−/− mice and B6 WT mice fed with HFD.

ATF3−/− mice displayed glucose intolerance as judged by intraperitoneal GTT (FIG. 3A) and decreased insulin sensitivity as judged by intraperitoneal ITT (FIG. 3B) as compared to WT mice. In addition, our data showed that glucose intolerance and decreased insulin sensitivity observed in ATF3−/− mice were improved after AAV-ATF3 treatment as compared to AAV-GFP group (control) (FIGS. 3C and 3D).

Example 4

Figure 4C:
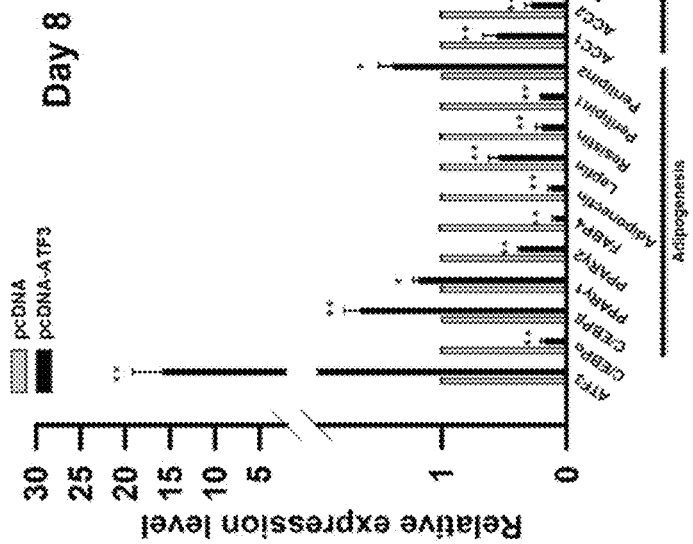
FIGS. 4 (A) to (E) show that impaired adipogenesis and activation of mitochondrial, brown or beige fat program in ATF3-overexpressing 3T3-L1 adipocytes. (A) Protein levels of ATF3 after transient transfection of ATF3 expression plasmid or ATF3-shRNA in 3T3-L1 preadipocytes. (B) Oil Red 0-staining of control and ATF3-overexpressing 3T3-L1 adipocytes on the $8^{th}$ day of differentiation. A light microscopy picture of the differentiated cells is shown. Scale bar=200 Relative quantification of adipocyte differentiation is also shown. (C) Relative adipogenic, lipogenic and lipolytic mRNA expression of C/EBPα, C/EBPβ, PPAR γ1, PPAR γ2, FABP4, adiponectin, leptin, Resistin, Perilipinl, Perilipin 2, ACC1, ACC2, FAS, DGAT1, DGAT2, SCD1, ChREBP, SREBP1, ATGL, HSL and MGL were measured by real time PCR on the $2^{nd}$ day of differentiation, normalized to GAPDH and relative to pcDNA control. (D) Relative adipogenic, lipogenic and lipolytic mRNA expression of C/EBPα, C/EBPβ, PPAR γ1, PPAR γ2, FABP4, adiponectin, leptin, Resistin, Perilipinl, Perilipin 2, ACC1, ACC2, FAS, DGAT1, DGAT2, SCD1, ChREBP, SREBP1, ATGL, HSL and MGL were measured by real time PCR on the $8^{th}$ day of differentiation, normalized to GAPDH and relative to pcDNA control. (E) Relative BAT, beige, mitochondria(M) and β-oxidation mRNA expression of UCP1, Prdm16, Dio2, Zic1, CIDEA, Elov13, CD137, Tbx1, CytC, COX4-1, COX4-2, Mcad, Cpt1α, HSP70 were measured by real time PCR on the $2^{rd}$ and $8^{th}$ day of differentiation, normalized to GAPDH and relative to pcDNA control.
Figure 4D:
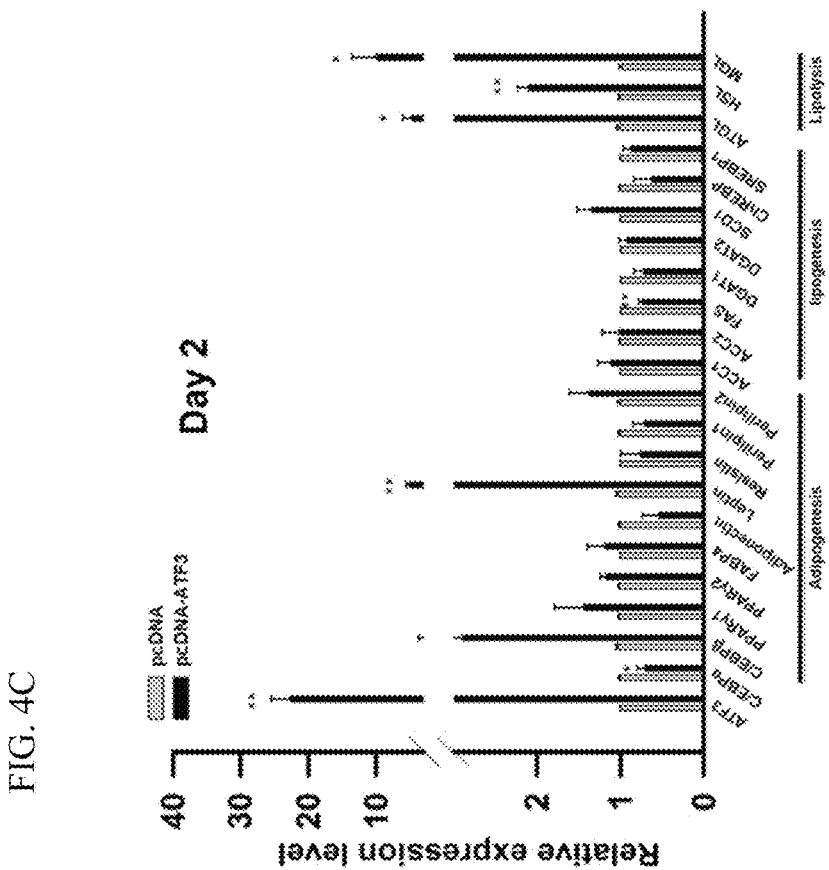
Figure 4E:
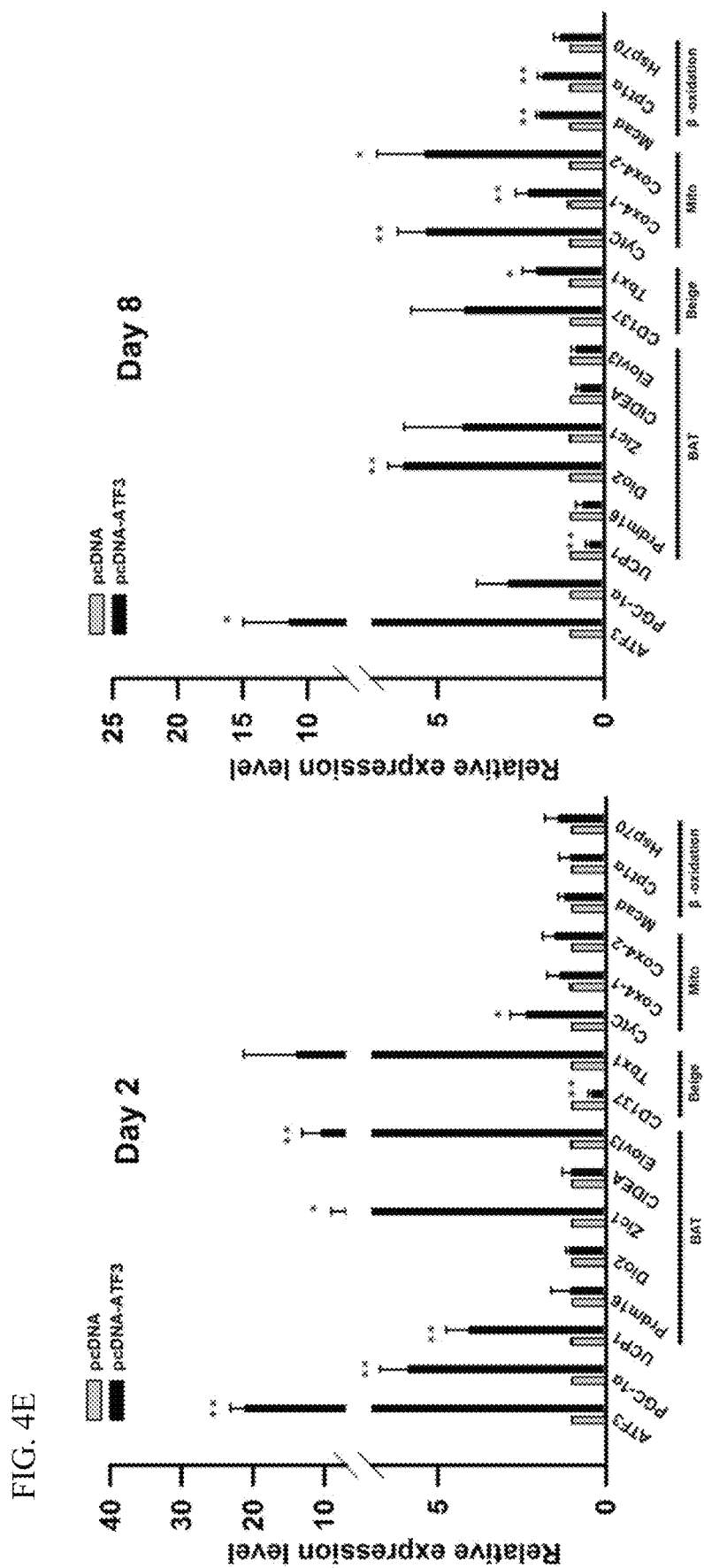

Overexpression of ATF3 Inhibits Differentiation and Induces Browning of 3T3-L1 Adipocytes We will further investigate the function of ATF-3 in 3T3-L1 adipocytes. Our data showed that expression level of ATF3 protein is low in 3T3-L1 preadipocytes (FIG. 4A). We will use ATF3 overexpression stable clone to examine the effect of ATF3 on adipocyte differentiation. ATF3-overexpressing adipocytes exhibited less lipid accumulation (Oil red O staining) (FIG. 4B) with diminished expression of adipogenic markers (including C/EBPα, PPARγ, FABP4, adiponectin, leptin, resistin and perilipin) and lipogenic markers (including ACC1, ACC2, FAS, DGAT1, DGAT2, SCD1, ChREBP, and SREBP1) as compared to the control cells on the $2^{nd}$ and $8^{th}$ day of differentiation (FIGS. 4C and 4D). To examine the effect of ATF3 on white-to-brown adipocyte transition in vitro. Our results indicated that BAT markers (UCP1, Prdm16, Dio2, Zic1, CIDEA, Elov13), beige markers (CD137, Tbx1), mitochondria gene (CytC, Cox4-1, Cox4-2) and β-oxidation gene (Mcad, Cpt1α, HSP70) are upregulated in ATF3 overexpressing 3T3-L1 cells as compared to pcDNA control cells on the $2^{nd}$ and $8^{th}$ day of differentiation (FIG. 4E).

Example 5

Figure 5A:
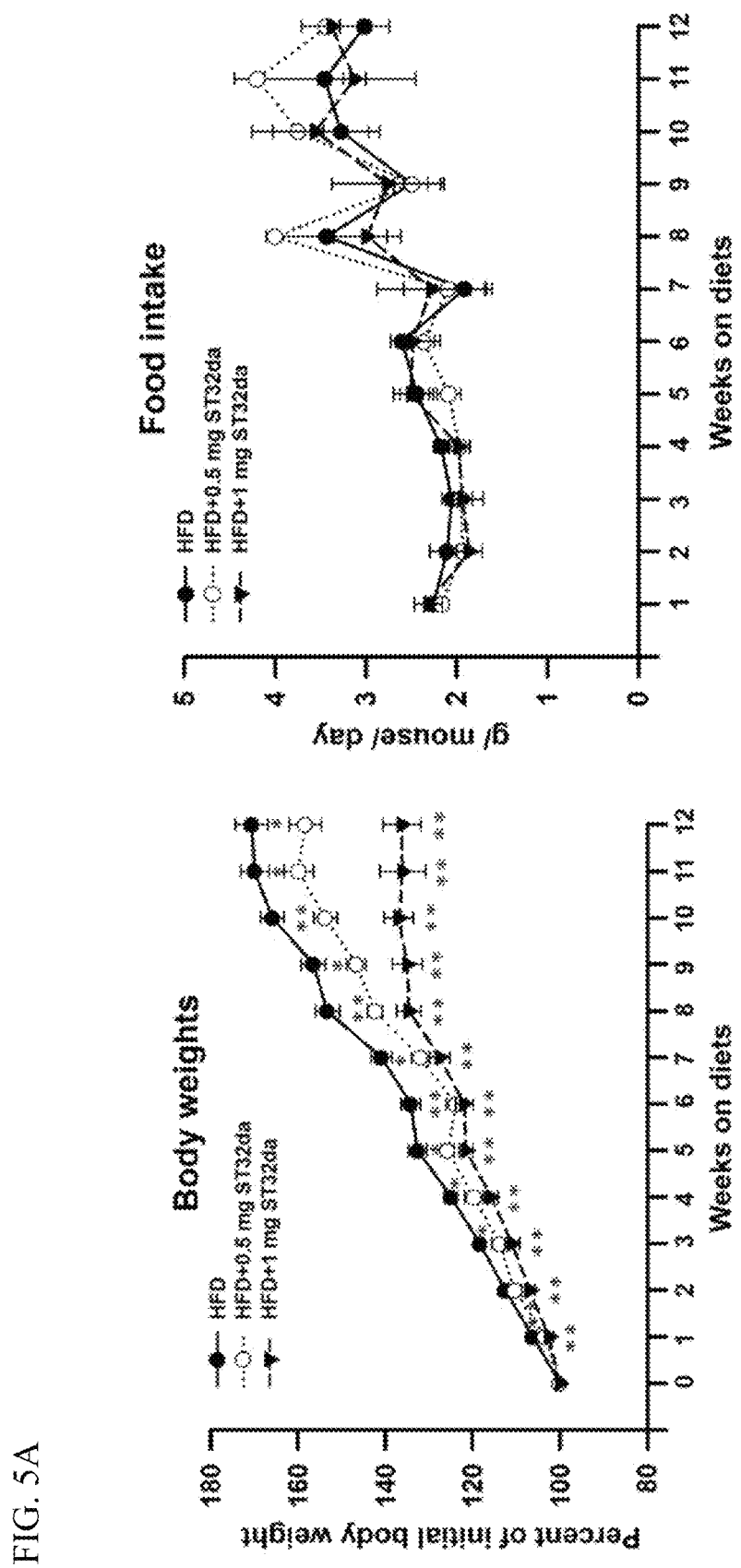
FIGS. 5 (A) to (E) show that ATF3 inducer ST32da prevents diet-induced obesity and improves metabolic dyshomeostasis in HFD fed wild type mice. Analysis of HFD-fed WT mice either without or treated with ATF3 inducer at dose of 0.5 mg/kg/day or 1 mg/kg/day. (A) Percent of initial body weight (left panel) and food intake (right panel). (B) Percent depot weights of inguinal (iWAT), epididymal (eWAT), mesenteric (mWAT), retroperitoneal (rWAT) and BAT fat depots. (C) liver weights. (D) glucose tolerance test. (E) insulin tolerance test.
Figure 5B:
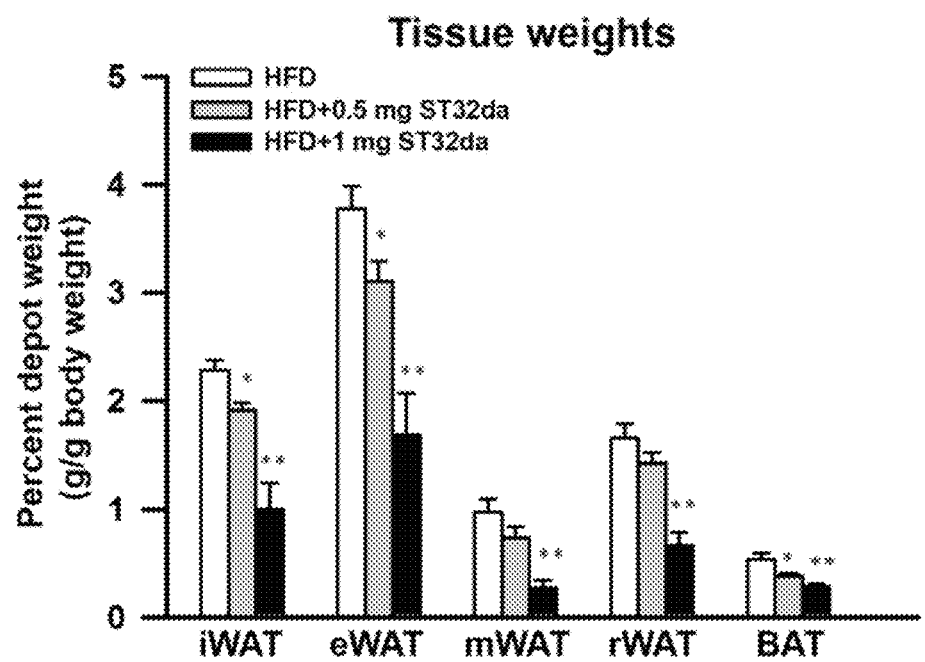
Figure 5C:
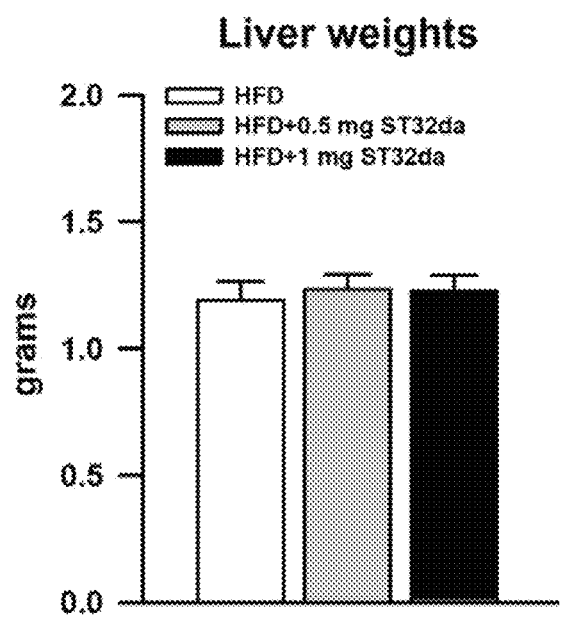
Figure 5D:
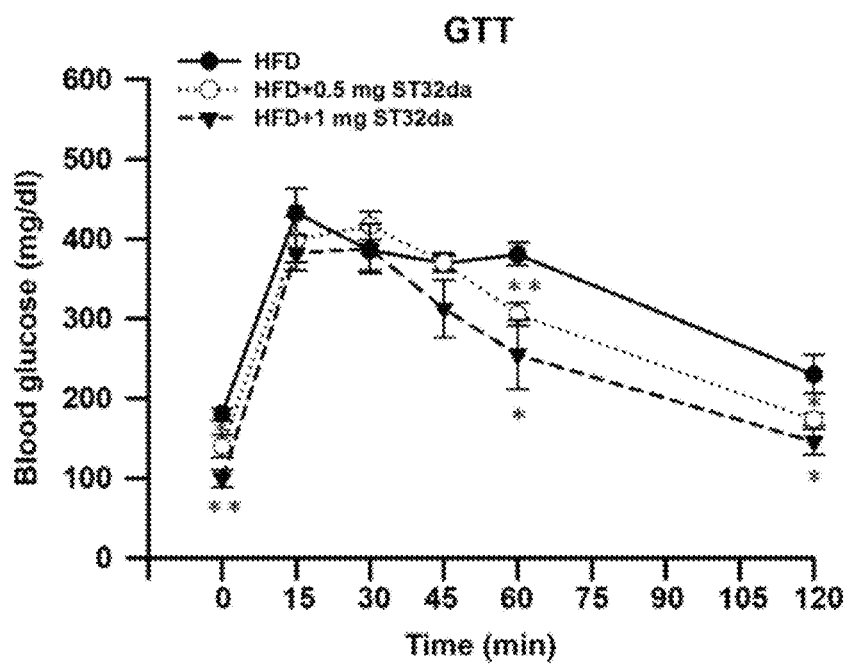
Figure 5E:
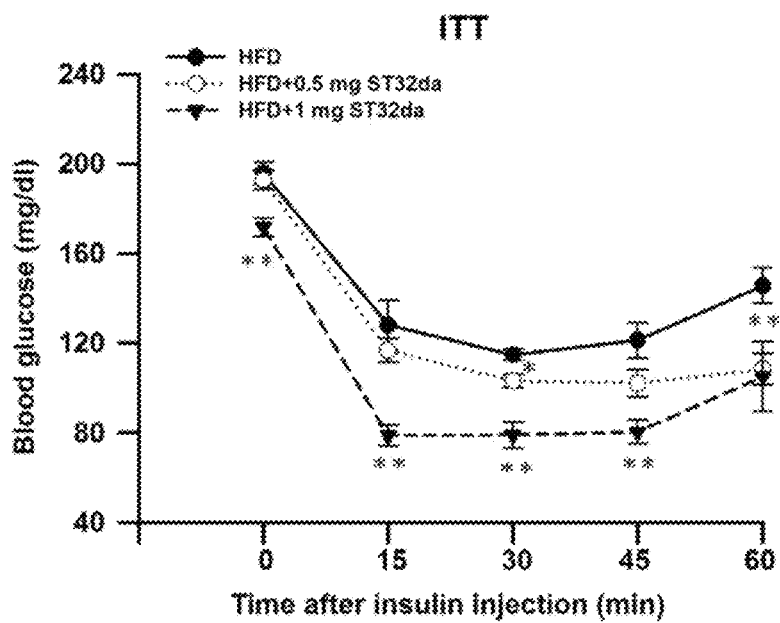

ATF3 Inducer ST32da Prevents Diet-Induced Obesity and Improves Dysregulated Metabolism To further investigate the physiological implications of the metabolic reprogramming induced by ATF3 inducer ST32da, we assessed the effect of ST32da administration on obesity. As shown in FIG. 5A, ST32da treatment could prevent HFD-induced obesity (FIG. 5A, left panel), without affecting their food intake (FIG. 5A, right panel). Consistent with this reduction, we observed decreased adipose depot mass including iWAT, eWAT, mWAT, rWAT and BAT in ST32da-treated group (FIG. 5B). In addition, ST32da treatment did not affect liver weights (FIG. 5C). Further evidence of improved metabolic profiles in ST32da-treated mice was the enhanced glucose tolerance (FIG. 5D) and improved inulin sensitivity (FIG. 5E).

Example 6

ATF3 Inducers ST32da, ST32db and ST32c Improve Heart Function after High Pressure Induced Heart Failure The treatment with ATF3 inducers ST32da, ST32db and ST32c attenuated TAB-induced LV dilatation and increased contractility in mice. The experimental timeline for TAB and ST32da therapy was as follows. Mice were pre or post treated with intraperitoneal ST32da (0.2 mg/kg) twice a week from $4^{th}$ to $10^{th}$ week after TAB procedure. Echocardiographic measurements were performed on mice before (week 4) and after (week 10) ST32da, ST32db, ST32c therapy in both the procedure group and the nonprocedure group. Parameters, including interventricular septum thickness at diastole (IVSd) and systole (IVSs), left ventricular internal diameter at diastole (LVIDd) and systole (LVIDs), left ventricular posterior wall thickness at diastole (LVPWd) and systole (LVPWs), fractional shortening of left ventricle, ejection fraction of left ventricle (EF), and heart rate (HR) are shown.

| | Heart Rate | IVSd (mm) | LVIDd (mm) | LVPWd (mm) | IVSs (mm) | LVIDs (mm) | LVPWs (mm) | EF (%) | FS (%) |
|---|---|---|---|---|---|---|---|---|---|
| sham (n = 6) | 308.667 ± 12.580 | 0.767 ± 0.047 | 3.867 ± 0.074 | 0.800 ± 0 | 1.283 ± 0.687 | 2.317 ± 0.203 | 1.283 ± 0.068 | 76.333 ± 5.467 | 39.667 ± 4.955 |
| ST32c sham (n = 3) | 318.667 ± 10.656 | 0.800 ± 0 | 3.733 ± 0.047 | 0.800 ± 0 | 1.367 ± 0.082 | 2.200 ± 0.047 | 1.333 ± 1.633 | 79.000 ± 1.633 | 41.333 ± 1.700 |
| ST32da sham (n = 3) | 303.667 ± 29.409 | 0.767 ± 0.047 | 3.833 ± 0.094 | 0.800 ± 0 | 1.400 ± 0.082 | 2.133 ± 0.236 | 1.400 ± 0.141 | 81.000 ± 4.967 | 44.000 ± 4.967 |
| ST32db sham (n = 3) | 318.500 ± 14.500 | 0.800 ± 0 | 4.067 ± 0.249 | 0.800 ± 0 | 1.533 ± 0.094 | 2.233 ± 0.170 | 1.433 ± 0.124 | 81.667 ± 2.867 | 44.667 ± 2.867 |
| TAB (n = 3) | 330.333 ± 19.32 | 1.125 ± 0.205 | 4.000 ± 0.173 | 0.900 ± 0.071 | 1.600 ± 0.245 | 2.725 ± 0.130 | 1.350 ± 0.087 | 66.250 ± 1.090 | 31.250 ± 0.433 |
| ST32c TAB (n = 3) | 340.000 ± 45 | 1.350 ± 0.050 | 3.350 ± 0.250 | 1.350 ± 0.150 | 1.950 ± 0.05 | 1.700 ± 0.200 | 2.000 ± 0.200 | 86.500 ± 1.500 | 54.500 ± 3.500 |
| ST32da TAB (n = 2) | 294.000 ± 0 | 1.200 ± 0 | 3.600 ± 0 | 1.000 ± 0 | 1.600 ± 0 | 2.500 ± 0 | 1.600 ± 0 | 75.000 ± 0 | 41.000 ± 0 |
| ST32db TAB (n = 4) | 301.000 ± 5.715 | 1.050 ± 0.150 | 3.600 ± 0.141 | 1.050 ± 0.112 | 1.750 ± 0.1658 | 1.850 ± 0.206 | 1.700 ± 0.158 | 84.750 ± 3.448 | 48.250 ± 3.767 |

Example 7

ATF3 Inducer ST32db Prevents Diet-Induced Obesity

Figure 6A:
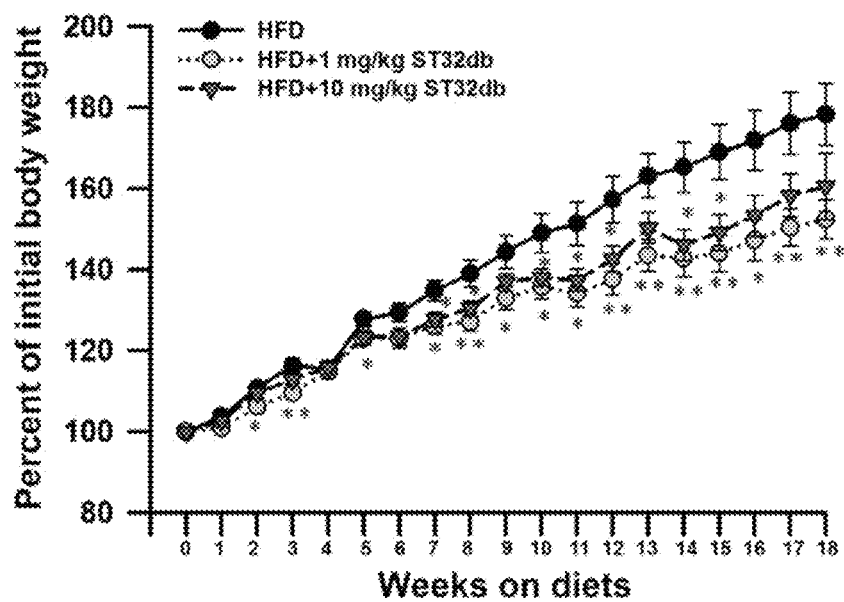
FIGS. 6 (A) and (B) show that ATF3 inducer ST32db prevents diet-induced obesity in HFD-fed wild type mice. Analysis of HFD-fed mice either without or treated with ATF3 inducer ST32db at dose of 1 or 10 mg/kg/day. (A) body weight. (B) food intake.
Figure 6B:
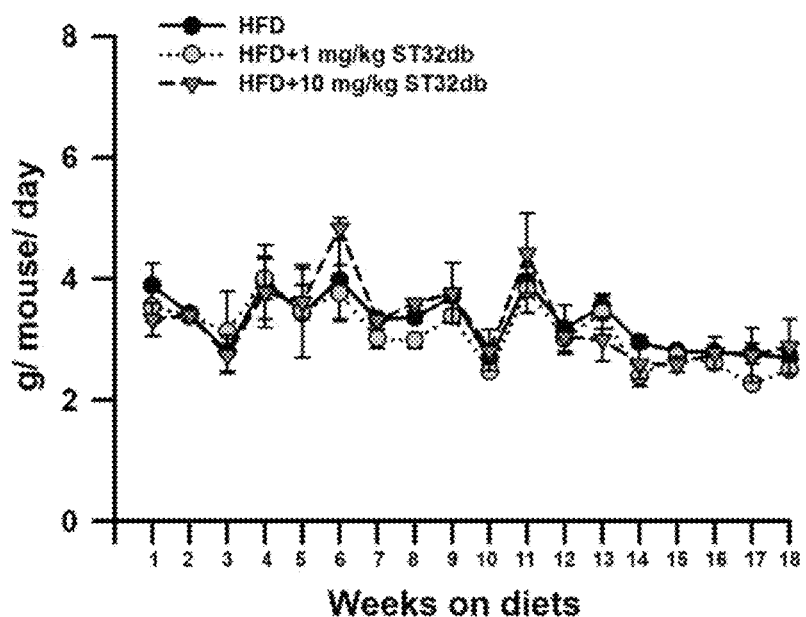

To investigate the physiological implications of the metabolic reprogramming induced by ATF3 inducer ST32db, we assessed the effect of ST32db administration on obesity. As shown in FIG. 6A, ST32db treatment at the dose of 1 or 10 mg/kg/day could prevent HFD-induced obesity (FIG. 6A), without affecting their food intake (FIG. 6B).

Example 8

ATF3 Inducer ST32c Prevents Diet-Induced Obesity

Figure 7:
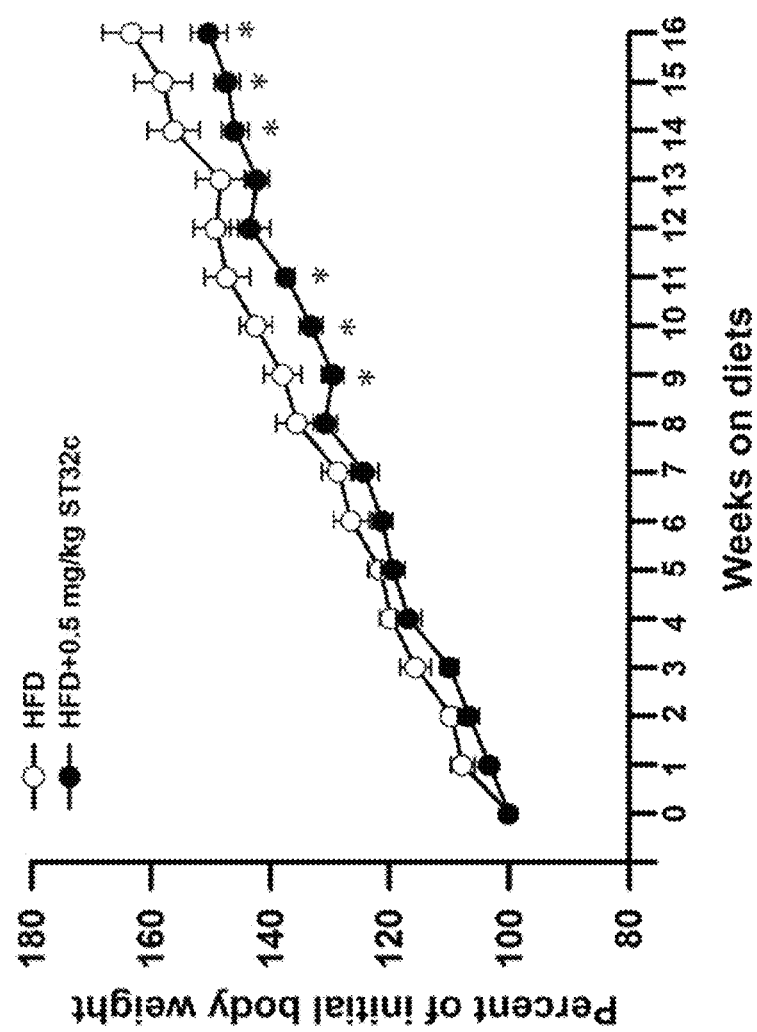
FIG. 7 shows that ATF3 inducer, ST32c, prevents diet-induced obesity in HFD-fed wild type mice. Body weight measurement of HFD-fed mic either without or treated with ATF3 inducer ST32c at dose of 0.5 mg/kg/day.

To investigate the physiological implications of the metabolic reprogramming induced by ATF3 inducer ST32c, we assessed the effect of ST32c administration on obesity. As shown in FIG. 7, ST32c treatment at the dose of 0.5 /mg/kg/day could prevent HFD-induced obesity (FIG. 7).

We claim:

1. A compound having formula (I),

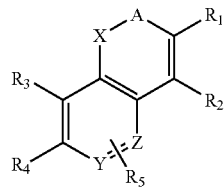

wherein
A is C(=O)— or —C(=S)—;
X is —O—;
Y is —C—;
Z is —C— or —C(=O)—;
$R_1$ and $R_2$ are taken together with their intervening atoms to form an oxolane, and wherein the oxolane is substituted by alkyl at the 2-position, and optionally substituted by alkyl at the 1-position;
$R_3$ and $R_4$ are taken together with their intervening atoms to form an optionally substituted fused benzene ring, wherein the substituent is selected from $NH_2$, halogen, hydroxy, alkyl, haloalkyl, hydroxyalkyl, alkoxy, alkoxyalkyl, alkenyl alkynyl, aryl or heteroaryl,
wherein the substituent alkyl of the oxolane is $C_{1-4}$ alkyl; and
$R_5$ is H, halogen, —OH, —$NO_2$, alkyl, haloalkyl, hydroxyalkyl, alkoxy, alkoxyalkyl, alkenyl or alkynyl;
or a tautomer, enantiomer, stereoisomer thereof, or a pharmaceutically acceptable salt thereof.

2. The compound of claim 1, wherein $R_1$ and $R_2$ are taken together with their intervening atoms to form an oxolane ring, wherein the ring is substituted by two alkyl substituents at the 2- and 1-positions.

3. The compound of claim 1, wherein the $C_{1-4}$ alkyl is methyl.

4. The compound of claim 1, wherein the fused benzene ring formed by $R_3$ and $R_4$ is substituted by OH, $NH_2$, $NO_2$, $C_{1-4}$alkyloxy, halogen or aryl.

5. The compound of claim 1, wherein $R_5$ is OH, $C_{1-4}$alkoxyl, $NO_2$, halogen, $C_{1-4}$alkyl or phenyl.

6. A compound selected from the group consisting of:
ST32c: 2-methyl-1H-benzo[h]furo[3,2-c]chromen-11 (2H)-one;

ST32da: (1R,2S)-1,2-dimethyl-1H-benzo[h]furo[3,2-c]chromen-11(2H)-one;

ST32da': (1R,2R)-5-chloro-1,2-dimethyl-1,2-dihydro-11H-benzo[h]furo[3,2-c]chromen-11-one;

ST32db: (1R,2R)-1,2-dimethyl-1H-benzo[h]furo[3,2-c]chromen-11(2H)-one;

ST32BA: (1R,2S)-1,2,6-trimethyl-1,2-dihydro-11H-benzo[h]furo[3,2-c]chromen-11-one;

6c: (1R,2S)-5-bromo-1,2-dimethyl-1,2-dihydro-11H-benzo[h]furo[3,2-c]chromen-11-one;

6c': (1R,2R)-5-bromo-1,2-dimethyl-1,2-dihydro-11H-benzo[h]furo[3,2-c]chromen-11-one;

11: (1R,2S)-1,2-dimethyl-1,2-dihydro-11H-benzo[h]furo[3,2-c]chromen-11-thione; and 11': (1R,2R)-1,2-dimethyl-1,2-dihydro-11H-benzo[h]furo[3,2-c]chromen-11-thione;

or a tautomer, enantiomer, stereoisomer thereof, or a pharmaceutically acceptable salt thereof.

7. A pharmaceutical or food composition comprising a compound of formula (I) according to claim 1 and a pharmaceutically acceptable carrier.

8. A method for (i) treating obesity, obesity-induced diabetes, or cardiomyopathy, or (ii) increasing heart function, comprising administering an effective amount of the compound of claim 1 to a subject, wherein the cardiomyopathy is induced by high blood pressure or hypoxia.

9. The method of claim 8, wherein the obesity is high fat food-induced obesity.

10. The method of claim 8, wherein the compound is in an amount ranging from 1 mg/kg/day to 2,000 mg/kg/day.

\* \* \* \* \*